United States Patent
Nishii

(10) Patent No.: US 10,188,364 B2
(45) Date of Patent: Jan. 29, 2019

(54) RADIATION IMAGING CONTROL APPARATUS, RADIATION IMAGING APPARATUS, AND STORAGE MEDIUM STORING PROGRAM

(71) Applicant: CANON KABUSHIKI KAISHA, Tokyo (JP)

(72) Inventor: Yuichi Nishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 256 days.

(21) Appl. No.: 15/075,907

(22) Filed: Mar. 21, 2016

(65) Prior Publication Data

US 2016/0287204 A1    Oct. 6, 2016

(30) Foreign Application Priority Data

Mar. 31, 2015   (JP) .................. 2015-072492

(51) Int. Cl.
*A61B 6/00* (2006.01)
(52) U.S. Cl.
CPC ............... *A61B 6/54* (2013.01); *A61B 6/563* (2013.01); *A61B 6/461* (2013.01)

(58) Field of Classification Search
None
See application file for complete search history.

(56) References Cited

U.S. PATENT DOCUMENTS

| | | | |
|---|---|---|---|
| 2004/0066900 | A1 | 4/2004 | Motoki |
| 2011/0148710 | A1 | 6/2011 | Smid et al. |
| 2014/0177804 | A1 | 6/2014 | Kobayashi et al. |
| 2014/0276056 | A1* | 9/2014 | Ohta ............... A61B 6/465 600/440 |

FOREIGN PATENT DOCUMENTS

| | | |
|---|---|---|
| JP | 4193444 B2 | 12/2008 |
| JP | 2014-121455 A | 7/2014 |

\* cited by examiner

*Primary Examiner* — Hoon Song
(74) *Attorney, Agent, or Firm* — Venable LLP

(57) ABSTRACT

To facilitate handling of an X-ray imaging system capable of selecting plural radiation imaging apparatuses, a radiation imaging control apparatus manages configuration information indicating whether a first communication unit of an X-ray imaging unit operates as a master unit or a slave unit, and transmits the configuration information to the X-ray imaging unit. The X-ray imaging unit selects whether to operate as the master unit or the slave unit according to the transmitted configuration information.

16 Claims, 17 Drawing Sheets

RADIATION IMAGING CONTROL APPARATUS, RADIATION IMAGING APPARATUS, AND STORAGE MEDIUM STORING PROGRAM

BACKGROUND OF THE INVENTION

Field of the Invention

The present invention particularly relates to a radiation imaging control apparatus and a radiation imaging apparatus which are suitably used to generate radiation images, and a storage medium which stores programs to operate these apparatuses.

Description of the Related Art

Recently, X-ray imaging systems have been utilized in various fields. Particularly, the X-ray imaging system is one of the important means for diagnosis in medical fields. More specifically, in the X-ray imaging system of the medical field, first, when an X-ray generated by an X-ray generating apparatus is irradiated from an X-ray irradiating unit to an object, the X-ray transmitted through the object is imaged by an X-ray imaging apparatus (so called an X-ray sensor), and thus an X-ray image is obtained. Then, the obtained X-ray image is subjected to an image process and the like, and the processed X-ray image is displayed on a monitor. In the X-ray imaging system of the medical field, the X-ray image displayed on the monitor in this manner is utilized for the diagnosis.

In the X-ray imaging system like this, there is the technique described in Japanese Patent No. 4193444 as the technique of selecting, from among plural X-ray imaging apparatuses, the X-ray imaging apparatus to be actually used for performing imaging.

In the technique described in Japanese Patent No. 4193444, when imaging is selected and instructed on the imaging instruction screen, the types (of the X-ray imaging apparatuses) capable of performing imaging of the imaging region indicated by the reservation information for the imaging are detected, and the plural type buttons respectively corresponding to the detected types capable of performing the imaging are displayed. Then, when any one of the plural type buttons is depressed, the type currently set in the reservation information for the imaging is changed to the type corresponding to the depressed type button.

However, in the technique described in Japanese Patent No. 4193444, the controller for performing the setting of the type to be used for the imaging is communicably connected to the plural X-ray imaging apparatuses via cables. For this reason, there is a problem that it is not easy to make the X-ray imaging apparatuses transportable. Besides, there is a problem that it is not easy to increase and decrease the number of the X-ray imaging apparatuses connected to the controller.

SUMMARY OF THE INVENTION

A radiation imaging control apparatus according to the present invention is characterized by comprising: a managing unit configured to, in a case where a radiation imaging apparatus performs wireless communication, manage wireless configuration information including information indicating whether to operate the radiation imaging apparatus as a master unit or a slave unit; and an output unit configured to output the wireless configuration information managed by the managing unit.

According to the present invention, it is possible to facilitate handling in a radiation imaging system capable of selecting plural radiation imaging apparatuses.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

Background to Embodiments

Before describing the embodiments, the background to the embodiments will be described hereinafter.

Figure 1:
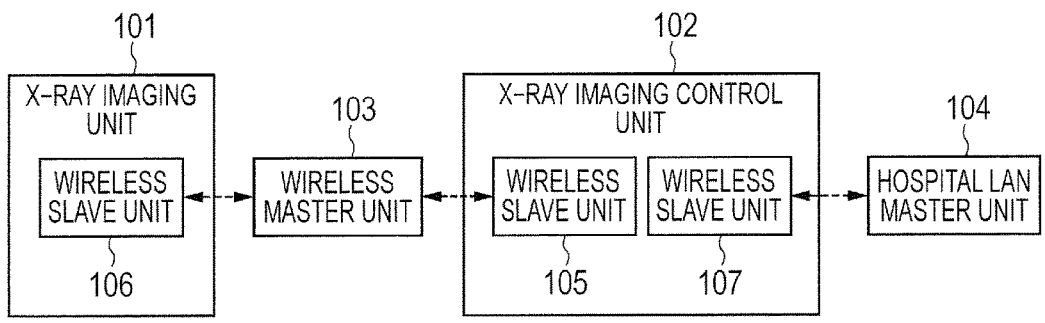
FIG. 1 is a block diagram for illustrating a first example of an X-ray imaging system.

FIG. 1 is a block diagram for illustrating a first example of an X-ray imaging system.

As described above, in the X-ray imaging system, an X-ray generated by an X-ray generating apparatus is first irradiated from an X-ray irradiating unit to an object, and the X-ray transmitted through the object is imaged by an X-ray imaging apparatus to obtain an X-ray image. Then, the obtained X-ray image is transmitted from the X-ray imaging apparatus to an X-ray imaging control unit, the transmitted X-ray image is subjected to an image process and the like, and the processed X-ray image is displayed on a monitor.

The X-ray imaging system of FIG. 1 comprises an X-ray imaging unit 101, an X-ray imaging control unit 102, a wireless master unit 103 and a hospital LAN (local area network) master unit 104.

FIG. 1 shows the example that, in the X-ray imaging system, the X-ray image is transferred from the X-ray imaging unit 101 to the X-ray imaging control unit 102 by using wireless communication via the wireless master unit 103. To facilitate handling of the X-ray imaging system, the X-ray imaging unit 101 and the X-ray imaging control unit 102 are communicably connected to each other by wireless communication.

In the example of FIG. 1, the wireless master unit 103 is provided, and the X-ray imaging unit 101 and the X-ray imaging control unit 102 are respectively connected to the wireless master unit 103 as the slave units. Therefore, in this case, the X-ray imaging control unit 102 is connected to all the X-ray imaging units (the X-ray imaging unit 101, etc.) connected to the wireless master unit 103, so that all the X-ray imaging units connected to the wireless master unit 103 can be used for performing imaging of the X-ray images. For this reason, even in a case where plural pieces of imaging reservation information for which the X-ray imaging units to be used are respectively different have been registered side by side, the X-ray imaging control unit 102 only has to select the target X-ray imaging unit from among the X-ray imaging units communicably connected to the X-ray imaging control unit 102. Therefore, the X-ray imaging control unit 102 need not switch the connections to the X-ray imaging units.

The X-ray imaging control unit 102 uses a wireless slave unit 105 built therein for communication with the X-ray imaging unit 101. On the other hand, the X-ray imaging unit 101 uses a wireless slave unit 106 built therein for communication with the X-ray imaging control unit 102. For example, a further slave unit can be added by using an AP (access point) connected to a USB (universal serial bus). A wireless slave unit 107 added in the X-ray imaging control unit 102 can be used for communication with the hospital LAN master unit 104. For example, an RIS (radiology information system), a PACS (picture archiving and communication system) or the like can be used as the hospital LAN master unit 104. Therefore, in the X-ray imaging system of FIG. 1, the X-ray imaging control unit 102 can have both the function to communicate with the X-ray imaging unit 101 and the function to communicate with the hospital LAN master unit 104.

However, in the X-ray imaging system of FIG. 1, since the three units of the X-ray imaging unit 101, the X-ray imaging control unit 102 and the wireless master unit 103 are necessary, there is a fear that the place where the wireless master unit 103 should be installed becomes a problem.

Figure 2:
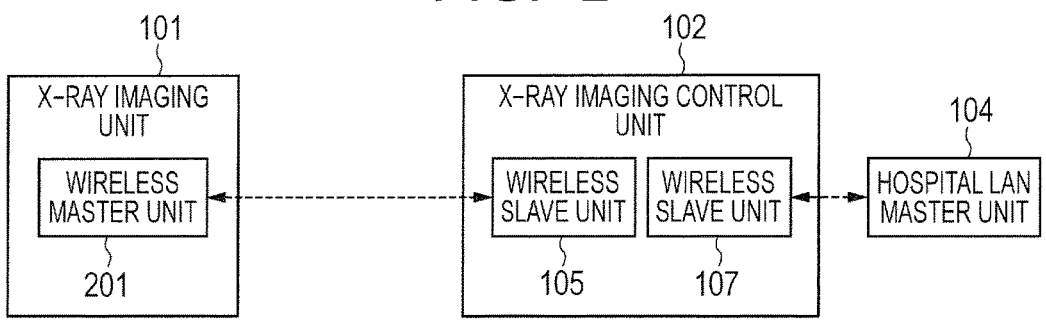
FIG. 2 is a block diagram for illustrating a second example of the X-ray imaging system.

Thus, it is conceivable to provide the X-ray imaging system as illustrated in FIG. 2. FIG. 2 is the block diagram for illustrating a second example of the X-ray imaging system. In FIG. 2, the portions same as those in FIG. 1 are respectively denoted by the corresponding same reference numerals as in FIG. 1, and the detailed descriptions of these portions will be omitted.

The X-ray imaging system of FIG. 2 comprises the X-ray imaging unit 101, the X-ray imaging control unit 102 and the hospital LAN master unit 104.

In the example of FIG. 2, the X-ray imaging unit 101 comprises a wireless master unit 201. The wireless master unit 201 of the X-ray imaging unit 101 communicates with the wireless slave unit 105 of the X-ray imaging control unit 102. In the example of FIG. 2, a communication unit (unit) performing communication as the wireless master unit is provided in the X-ray imaging unit 101. Therefore, the communication unit (unit) performing communication as the wireless master unit need not be handled as a unit different from the X-ray imaging unit 101. For this reason, the X-ray imaging unit 101 and the X-ray imaging control unit 102 can perform wireless communication with each other without using the wireless master unit 103. That is, although the three units are necessary in the example of FIG. 1, the two units are necessary in the example of FIG. 2. Therefore, in the X-ray imaging system of FIG. 2, the number of the units necessary for the wireless communication between the X-ray imaging unit 101 and the X-ray imaging control unit 102 can be reduced as compared with the X-ray imaging system of FIG. 1, so that it is possible to improve transportability of the X-ray imaging system.

Further, as well as the X-ray imaging system of FIG. 1, it is possible by using the wireless slave unit 107 added in the X-ray imaging control unit 102 to connect the X-ray imaging control unit 102 to the hospital LAN master unit 104 such as the RIS, the PACS or the like.

However, in the X-ray imaging system of FIG. 2, the X-ray imaging unit 101 has the function of the wireless master unit. Therefore, it is impossible, in the X-ray imaging system of FIG. 2, to achieve the constitution of the X-ray imaging system of FIG. 1 by which the X-ray imaging control unit 102 can connect to the plural X-ray imaging units at a time. Thus, for example, in such a case where the two or more X-ray imaging units are installed in visiting cars and the installed two or more X-ray imaging units are properly used depending on situations, it is necessary to properly switch the X-ray imaging units to connect to the X-ray imaging control unit 102.

Figure 3:
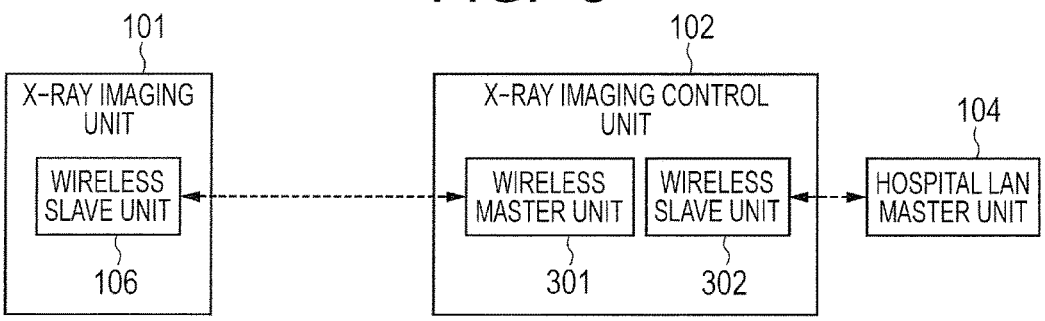
FIG. 3 is a block diagram for illustrating a third example of the X-ray imaging system.

Accordingly, it is conceivable to provide the X-ray imaging system as illustrated in FIG. 3. FIG. 3 is the block diagram for illustrating a third example of the X-ray imaging system. In FIG. 3, the portions same as those in FIG. 1 are respectively denoted by the corresponding same reference numerals as in FIG. 1, and the detailed descriptions of these portions will be omitted.

The X-ray imaging system of FIG. 3 comprises the X-ray imaging unit 101, the X-ray imaging control unit 102 and the hospital LAN master unit 104.

In the example of FIG. 3, the X-ray imaging control unit 102 comprises a wireless master unit 301 and a wireless slave unit 302. The wireless master unit 301 of the X-ray imaging control unit 102 communicates with the wireless slave unit 106 of the X-ray imaging control unit 101. Since a communication unit (unit) performing communication as the wireless master unit is provided in the X-ray imaging control unit 102, the communication unit (unit) performing communication as the wireless master unit need not be handled as a unit different from the X-ray imaging control unit 102. For this reason, as well as the X-ray imaging system of FIG. 2, the number of the units necessary for the wireless communication between the X-ray imaging unit 101 and the X-ray imaging control unit 102 is "two" in the X-ray imaging system of FIG. 3. Therefore, the number of the units necessary for the wireless communication between the X-ray imaging unit 101 and the X-ray imaging control unit 102 can be reduced as compared with the X-ray imaging system of FIG. 1, so that it is possible to improve transportability of the X-ray imaging system.

In the X-ray imaging system of FIG. 3, the X-ray imaging control unit 102 has the function as the wireless master unit.

Therefore, in the X-ray imaging system of FIG. 3, the X-ray imaging control unit 102 can connect at a time to the plural X-ray imaging units (the X-ray imaging unit 101, etc.), as well as the X-ray imaging system of FIG. 1.

Moreover, in the X-ray imaging system of FIG. 3, the X-ray imaging control unit 102 can connect to the hospital LAN master unit 104 such as the RIS, the PACS or the like, by using the wireless slave unit 302. However, in the X-ray imaging control unit 102, if the communication with the hospital LAN master unit 104 is once disconnected, the communication with the side of the wireless master unit 301 of the X-ray imaging control unit 102, i.e., the X-ray imaging unit 101, is once disconnected when the wireless slave unit 302 searches for the master unit. Thus, in the X-ray imaging system of FIG. 3, it is difficult to perform the simultaneous connection to both the X-ray imaging unit and the hospital LAN master unit, which can be achieved in the X-ray imaging systems of FIGS. 1 and 2.

The following embodiments are provided by considering the respective problems of the X-ray imaging systems illustrated in FIGS. 1 to 3. It should be noted that each of the following embodiments aims to make switching of the connection between the X-ray imaging control unit and the X-ray imaging unit unnecessary, improve the transportability of the X-ray imaging system, and adaptively satisfy the simultaneous connections of the X-ray imaging units and the hospital LAN master unit according to a use case or the like.

(Entire Configuration of X-Ray Imaging System)

Figure 4:
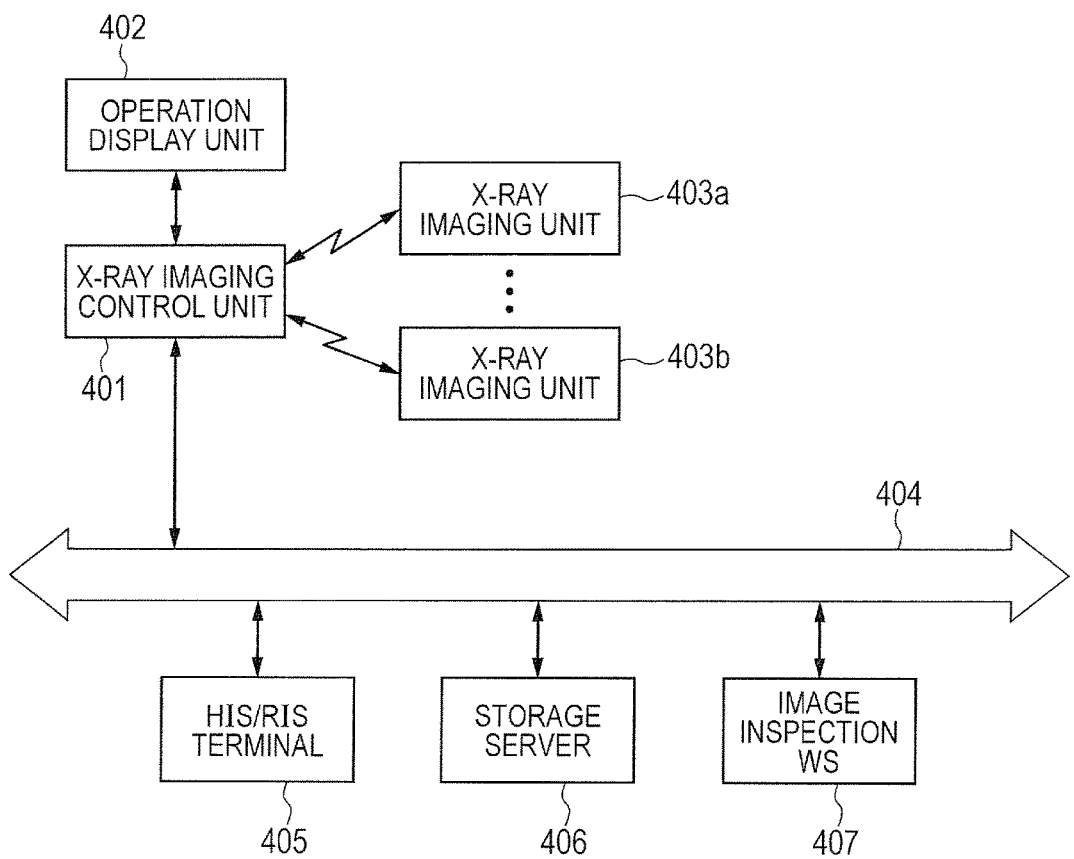
FIG. 4 is a diagram for illustrating the entire configuration of the X-ray imaging system.

FIG. 4 is a diagram for illustrating the entire configuration of the X-ray imaging system.

In FIG. 4, the X-ray imaging system comprises an X-ray imaging control unit 401, an operation display unit 402, X-ray imaging units 403a and 403b, an HIS/RIS terminal 405, a storage server 406 and an image inspection WS (work station) 407.

In the example of FIG. 4, the X-ray imaging control unit 401, which is an example of a radiation imaging control apparatus, is mutually and communicably connected to the HIS/RIS terminal 405, the storage server 406 and the image inspection WS 407, via a hospital LAN 404. Incidentally, the X-ray imaging control unit 401 may be mutually and communicably connected to the HIS/RIS terminal 405, the storage server 406 and the image inspection WS 407, via a communication path other than the hospital LAN 404, and, in this case, the communication path may be either a wired path or a wireless path.

The X-ray imaging control unit 401 controls the whole of the x-ray imaging system. In the example of FIG. 4, the X-ray imaging control unit 401 performs wireless communication with the plural X-ray imaging units 403a and 403b when controlling the plural X-ray imaging units 403a and 403b. The operation display unit 402 is connected to the X-ray imaging control unit 401.

The operation display unit 402 displays a GUI (graphical user interface) such as a console screen or the like to be used for controlling the whole of the X-ray imaging system, and images imaged and captured by the X-ray imaging units 403a and 403b. The operation display unit 402 accepts operations and character inputs by means of the buttons and the like displayed on the console thereof. As the operation display unit 402, a liquid crystal touch panel display is suitable due to its usage. However, the operation display unit 402 is not limited to the touch panel display. For example, a mobile PC (personal computer) or a tablet terminal having a liquid crystal touch panel display may be used as the operation display unit 402.

Each of the plural X-ray imaging units 403a and 403b, which is an example of a radiation imaging apparatus, performs imaging of the X-ray image obtained by irradiation with an X-ray tube and transmitted through the object, and outputs the digital data corresponding to the imaged X-ray image. The plural X-ray imaging units 403a and 403b are used to respectively perform imaging of, e.g., different regions of the object. Each of the X-ray imaging units 403a and 403b associates, e.g., imaging order information received from the external apparatus such as the X-ray imaging control unit 401, the HIS/RIS terminal 405 or the like before the imaging with the X-ray image after the imaging. The imaging order information includes, e.g., information of an object ID (identification), information of a region to be imaged, information of imaging date and time, and the like. Each of the X-ray imaging units 403a and 403b transmits the X-ray image, with which the imaging order information has been associated, to the X-ray imaging control unit 401. Moreover, each of the X-ray imaging units 403a and 403b outputs the X-ray image, with which the imaging order information has been associated, to the storage server 406 for storing the image and the image inspection WS 407 for performing the image process to the X-ray image to generate the final image to be used for diagnosis.

Incidentally, the HIS/RIS terminal 405, the storage server 406, the image inspection WS 407 and the hospital LAN 404 may not be included in the X-ray imaging system.

In the following respective embodiments, the functions to be used when the X-ray imaging control unit 401 and the X-ray imaging units 403a and 403b perform communication with the external apparatuses are mainly different from others. Therefore, in each of the following embodiments, only the constitution which works at the time when the X-ray imaging control unit 401 and the X-ray imaging units 403a and 403b perform communication with the external apparatuses will be described, and the descriptions for other constitutions will be omitted. Incidentally, in the plural X-ray imaging units 403a and 403b, the constitutions to be used for the communication with the external apparatuses can be achieved in the same way. Therefore, in each of the following embodiments, only a (single) X-ray imaging unit 403 will be used as a representative of the X-ray imaging units 403a and 403b in the X-ray imaging system.

First Embodiment

Initially, the first embodiment will be described.

Figure 5:
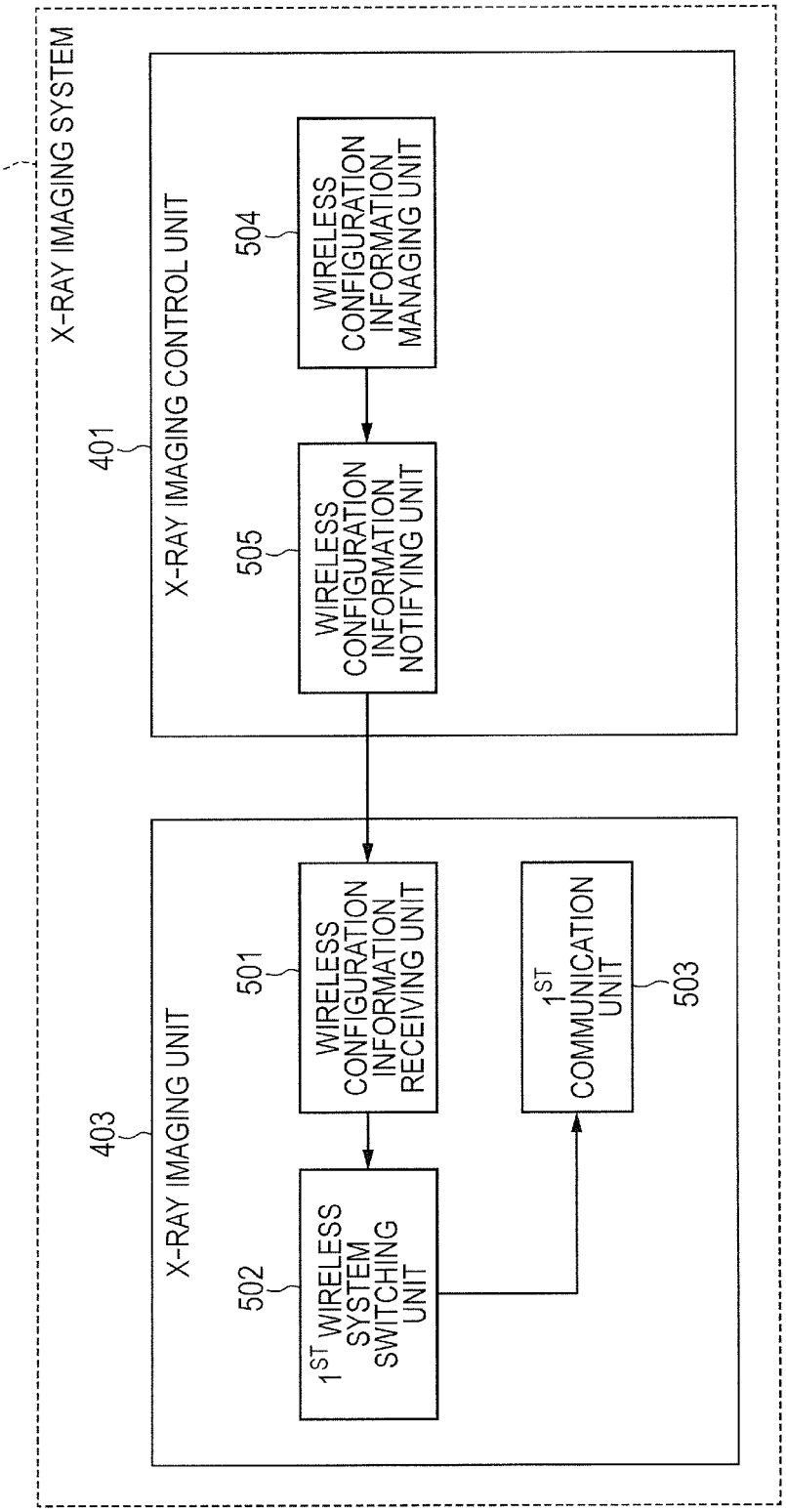
FIG. 5 is a block diagram for illustrating a fourth example of the X-ray imaging system.

FIG. 5 is a block diagram for illustrating an example of the configuration of an X-ray imaging system 500 according to the present embodiment. The X-ray imaging system 500 of FIG. 5 comprises the X-ray imaging control unit 401 and the X-ray imaging unit 403. The X-ray imaging unit 403 comprises a wireless configuration information receiving unit 501, a first wireless system switching unit 502 and a first communication unit 503. The X-ray imaging control unit 401 comprises a wireless configuration information managing unit 504 and a wireless configuration information notifying unit 505.

Figure 6:
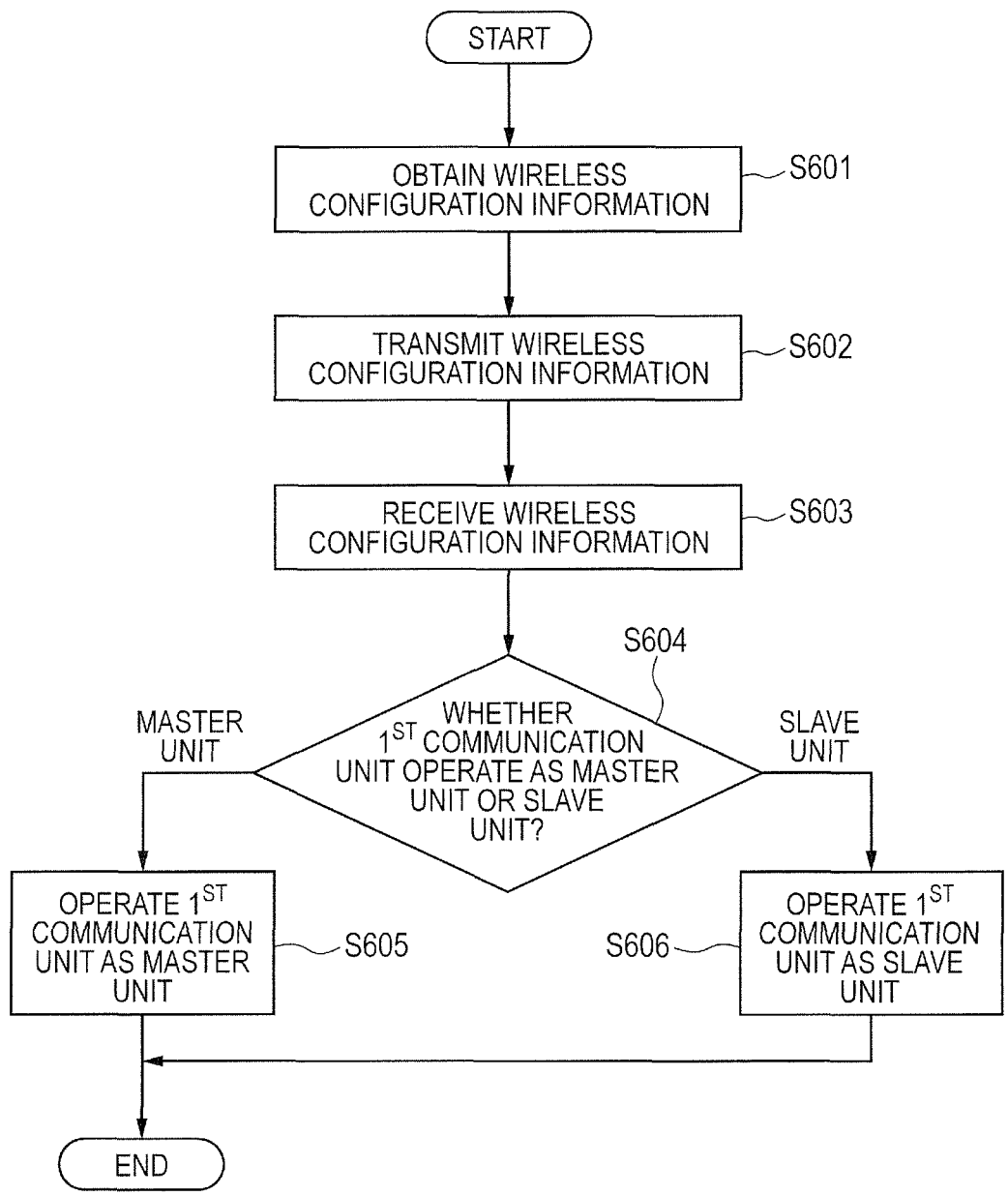
FIG. 6 is a flow chart for describing a first example of the operation of the X-ray imaging system.

FIG. 6 is a flow chart for describing an example of the operation of the X-ray imaging system 500. Hereinafter, the examples of the configuration and the process of the X-ray imaging system 500 will be described with reference to FIGS. 5 and 6.

The wireless configuration information managing unit 504 of the X-ray imaging control unit 401 manages wireless configuration information. The wireless configuration information in the present embodiment includes configuration information indicating whether the first communication unit 503 of the X-ray imaging unit 403 operates as a master unit or a slave unit, and information necessary for the X-ray imaging unit 403 to perform the communication with the X-ray imaging control unit 401. Here, the information necessary when the X-ray imaging unit 403 performs the communication with the X-ray imaging control unit 401 is, e.g., an SSID (service set identifier) and an encryption (cipher) key. The wireless configuration information is set based on, e.g., a user's input operation to the GUI displayed on the operation display unit 402. However, the method of setting the wireless configuration information is not limited to the above method using the GUI. For example, the X-ray imaging control unit 401 may obtain and set the wireless configuration information by previously performing the communication with the external apparatus. The wireless configuration information managing unit 504 stores the thus obtained wireless configuration. When there are the plural X-ray imaging units 403 in the X-ray imaging system, the wireless configuration information is individually managed for each of the x-ray imaging units 403. In this case, the discrimination information of each of the X-ray imaging units 403 is associated with the corresponding wireless configuration information.

The wireless configuration information notifying unit 505 obtains the wireless configuration information managed by the wireless configuration information managing unit 504 (S601). Next, the wireless configuration information notifying unit 505 transmits the wireless configuration information obtained in S601 to the X-ray imaging unit 403 (S602). When there are the plural X-ray imaging units 403 in the X-ray imaging system, the destination of the wireless configuration information is determined based on the discrimination information of the X-ray imaging unit 403 associated with the relevant wireless configuration information. When the X-ray imaging control unit 401 performs the wireless communication with the plural X-ray imaging units 403 and the X-ray imaging control unit 401 serves as the master unit, all the plural X-ray imaging units 403 serve as the slave units. However, the X-ray imaging control unit 401 may be configured to serve as the master unit in regard to a certain X-ray imaging unit and serve as the slave unit in regard to another X-ray imaging unit.

Next, the wireless configuration information receiving unit 501 of the X-ray imaging unit 403 receives the wireless configuration information transmitted from the wireless configuration information notifying unit 505 (S603). Then, based on the wireless configuration information received in S603, the first wireless system switching unit 502 determines whether the first communication unit 503 operates as the master unit or the slave unit (S604). When the first communication unit 503 operates as the master unit, the first wireless system switching unit 502 sets the first communication unit 503 to operate as the master unit (S605). Thus, when performing the wireless communication with the external apparatus, the X-ray imaging unit 403 serves as the master unit. On the other hand, when the first communication unit 503 operates as the slave unit, the first wireless system switching unit 502 sets the first communication unit 503 to operate as the slave unit (S606). Thus, when performing the wireless communication with the external apparatus, the X-ray imaging unit 403 serves as the slave unit. Here, the external apparatus may be the X-ray imaging control unit 401 or the apparatus other than the X-ray imaging control unit 401. As just described, the X-ray imaging unit 403 in the present embodiment has both the function of the wireless master unit and the function of the wireless slave unit.

The communication means between the wireless configuration information notifying unit 505 and the wireless configuration information receiving unit 501 may be a wired communication means using a LAN cable or the like, a communication means using infrared communication, or a wireless communication means using Bluetooth™ communication. When the wired communication means using the LAN cable is used, for example, the X-ray imaging units 403a and 403b can be connected to the hospital LAN 404 in the configuration of FIG. 4.

As just described, in the present embodiment, the X-ray imaging control unit 401 manages the configuration information indicating whether the first communication unit 503 of the X-ray imaging unit 403 operates as the master unit or the slave unit, and transmits the configuration information to the X-ray imaging unit 403. The X-ray imaging unit 403 selects whether to operate as the master unit or the slave unit, in response to the transmitted configuration information. Therefore, it is possible to facilitate handling of the X-ray imaging system. More specifically, it is possible to make the transportability of the apparatus constituting the X-ray imaging system easy, and it is possible to easily increase and decrease the number of the X-ray imaging units 403. Besides, when the two or more X-ray imaging units 403 are operated as the slave units, it becomes unnecessary to switch the X-ray imaging unit 403 to be connected to the X-ray imaging control unit 401. Moreover, in such a case, it is possible to perform the simultaneous connection to both the X-ray imaging unit 403 of the X-ray imaging control unit 401 and the hospital LAN master unit.

Second Embodiment

Subsequently, the second embodiment will be descried. The present embodiment has been accomplished by adding, to the first embodiment, the point of switching whether, in addition to the X-ray imaging unit 403, the X-ray imaging control unit 401 operates as the master unit or the slave unit. Therefore, in the present embodiment, the portions same as those already described in the first embodiment are respectively denoted by the corresponding same reference numerals illustrated in FIGS. 5 and 6, and the detailed descriptions thereof will be omitted.

Figure 7:
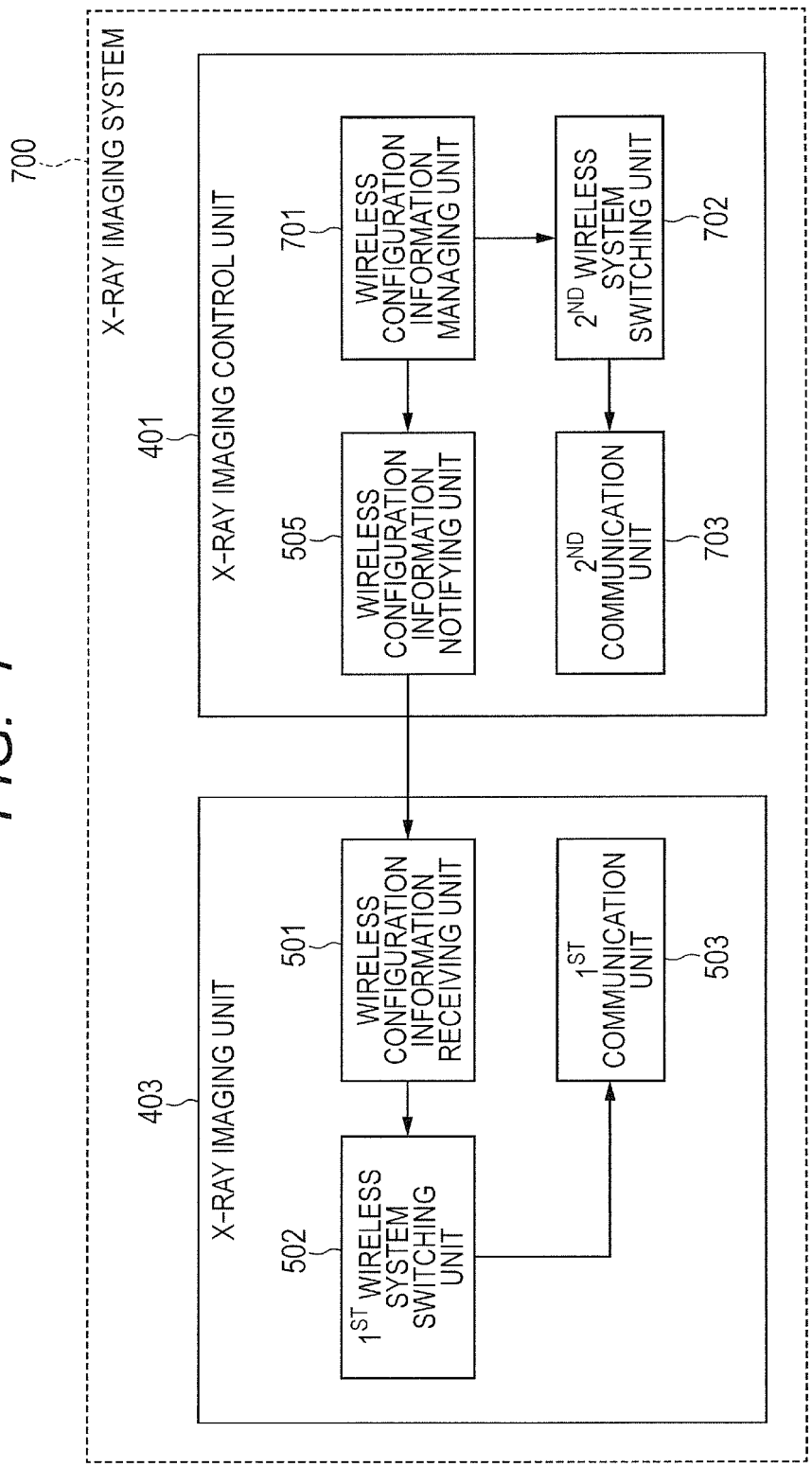
FIG. 7 is a block diagram for illustrating a fifth example of the X-ray imaging system.

FIG. 7 is a block diagram for illustrating an example of the configuration of an X-ray imaging system 700 according to the present embodiment. The X-ray imaging system 700 of FIG. 7 comprises the X-ray imaging control unit 401 and the X-ray imaging unit 403. The X-ray imaging unit 403 comprises the wireless configuration information receiving unit 501, the first wireless system switching unit 502 and the first communication unit 503. The X-ray imaging control unit 401 comprises the wireless configuration information notifying unit 505, a wireless configuration information managing unit 701, a second wireless system switching unit 702 and a second communication unit 703.

Figure 8:
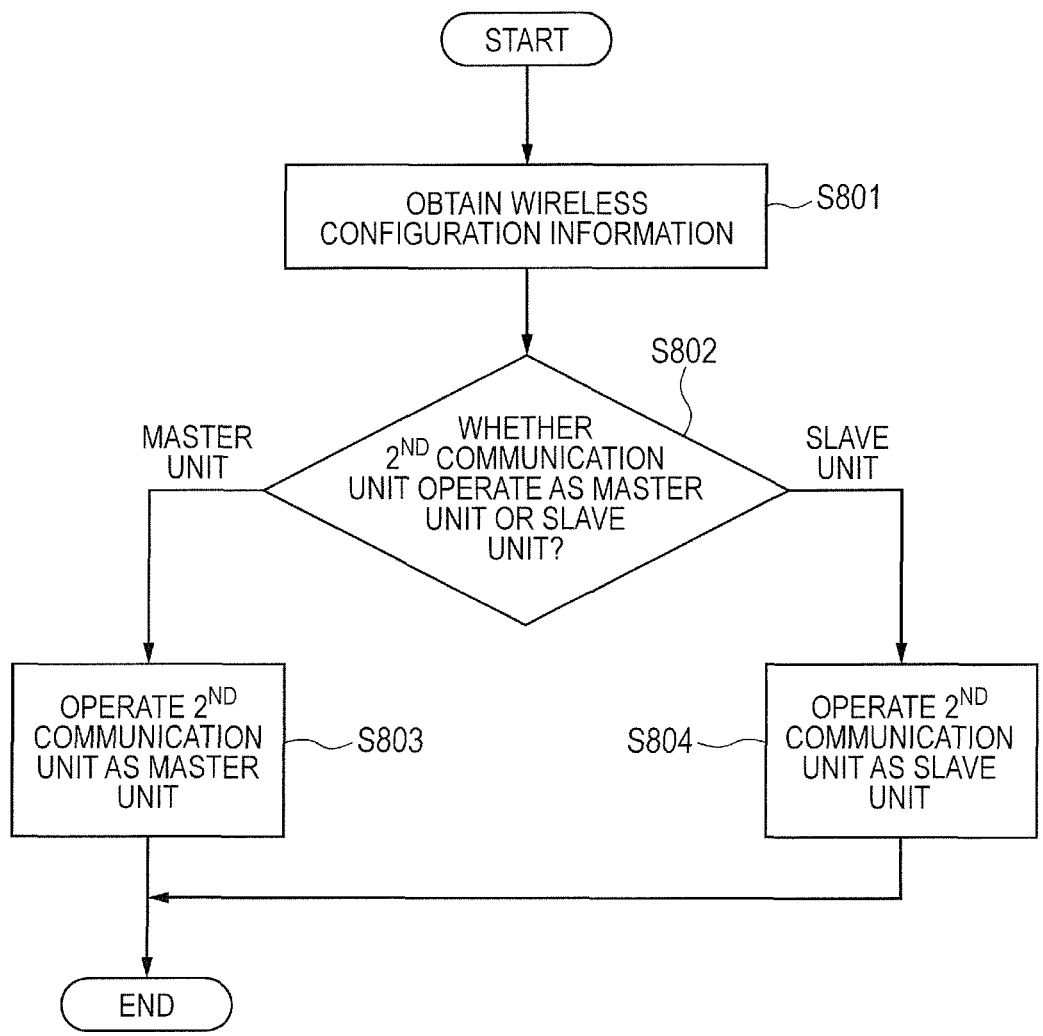
FIG. 8 is a flow chart for describing a second example of the operation of the X-ray imaging system.

FIG. 8 is a flow chart for describing an example of the operation of the X-ray imaging system 700. Hereinafter, the examples of the configuration and the process of the X-ray imaging system 700 will be described with reference to FIGS. 7 and 8.

The wireless configuration information managing unit 701 of the X-ray imaging control unit 401 manages, as configuration information, information indicating whether the first communication unit 503 of the X-ray imaging unit 403 operates as the master unit or the slave unit, and information indicating whether the second communication unit 703 of the X-ray imaging control unit 401 operates as the master unit or the slave unit. Moreover, the wireless configuration information managing unit 701 manages the information necessary when the first communication unit 503 and the second communication unit 703 perform mutual communication. Here, the information which is necessary when the first communication unit 503 and the second communication unit 703 perform the mutual communication is, e.g., an SSID and an encryption key.

The wireless configuration information of the present embodiment includes the above information. For example, the wireless configuration information is input based on a user's input operation using the operation display unit 402. At this time, one of the second communication unit 703 of the X-ray imaging control unit 401 and the first communication unit 503 of the X-ray imaging unit 403 is set to serve as the master unit and the other thereof is set to serve as the slave unit. For example, the operation display unit 402 displays the GUI for selecting whether to operate the second communication unit 703 of the X-ray imaging control unit 401 as the master unit or the slave unit. When it is selected to operate the second communication unit 703 of the X-ray imaging control unit 401 as the master unit, the configuration information is the information indicating that the second communication unit 703 of the X-ray imaging control unit 401 operates as the master unit and the first communication unit 503 of the X-ray imaging unit 403 operates as the slave unit. On the other hand, when it is selected to operate the second communication unit 703 of the X-ray imaging control unit 401 as the slave unit, the configuration information is the information indicating that the second communication unit 703 of the X-ray imaging control unit 401 operates as the slave unit and the first communication unit 503 of the X-ray imaging unit 403 operates as the master unit.

Incidentally, the method of setting the configuration information is not limited to the above method using the GUI. For example, the X-ray imaging control unit 401 may obtain and set the configuration information by previously performing communication with the external apparatus.

As described in the first embodiment, when there are the plural X-ray imaging units 403 in the X-ray imaging system, the wireless configuration information is individually managed for each of the x-ray imaging units 403. In this case, the discrimination information of each of the X-ray imaging units 403 is associated with the corresponding wireless configuration information.

Here, since the operation of the X-ray imaging system 700 at the time when switching the operation of the first communication unit 503 is achieved by the operation in S601 to S606 of FIG. 6 described in the first embodiment, the detailed description thereof will be omitted. On the other hand, the operation of the X-ray imaging system 700 at the time of switching the operation of the second communication unit 703 is as below.

The second wireless system switching unit 702 obtains the wireless configuration information from the wireless configuration information managing unit 701 (S801). Next, the second wireless system switching unit 702 determines whether the second communication unit 703 operates as the master unit or the slave unit, based on the wireless configuration information obtained in S801 (S802). Then, when the second communication unit 703 operates as the master unit, the second wireless system switching unit 702 sets the second communication unit 703 to operate as the master unit (S803). Thus, when performing the wireless communication with the X-ray imaging unit 403, the X-ray imaging control unit 401 serves as the master unit. In this case, in the flow chart of FIG. 6, the X-ray imaging unit 403 serves as the slave unit when performing the wireless communication with the X-ray imaging control unit 401.

On the other hand, when the second communication unit 703 operates as the slave unit, the second wireless system switching unit 702 sets the second communication unit 703 to operate as the slave unit (S804). Thus, when performing the wireless communication with the X-ray imaging unit 403, the X-ray imaging control unit 401 serves as the slave unit. In this case, in the flow chart of FIG. 6, the X-ray imaging unit 403 serves as the master unit when performing the wireless communication with the X-ray imaging control unit 401. As just described, the X-ray imaging control unit 401 in the present embodiment has both the function of the wireless master unit and the function of the wireless slave unit.

When the first communication unit 503 operates as the master unit and the second communication unit 703 operates as the slave unit, the first communication unit 503 starts the X-ray imaging unit 403 as the master unit, by using the SSID and the encryption key obtained by the wireless configuration information managing unit 701. On the other hand, the second communication unit 703 searches for the master unit by using the SSID and the encryption key obtained by the wireless configuration information managing unit 701, and thus establishes the communication with the master unit. After the communication is established, a control command and the like from the X-ray imaging control unit 401 are input from the second communication unit 703 to the X-ray imaging unit 403 via the first communication unit 503. The X-ray imaging unit 403 comes into the state capable of performing imaging of an X-ray image, based on the control command. After then, X-rays are irradiated, the X-ray image is imaged by the X-ray imaging unit 403, and the digital data of the X-ray image is thus generated. Then, the digital data of the X-ray image is transmitted from the first communication unit 503 to the X-ray imaging control unit 401 via the second communication unit 703. The X-ray imaging control unit 401 performs processes to the digital data of the X-ray image, and displays the X-ray image on the operation display unit 402.

As well as the first embodiment, the wireless configuration information managing unit 701 can individually manage the wireless configuration information for each of the plural x-ray imaging units 403. However, when the second communication unit 703 serves as the slave unit, the wireless configuration information managing unit can establish the communication with only the single X-ray imaging unit 403 at a time. Therefore, it is necessary for the second communication unit 703 not to simultaneously establish the communication with the plural X-ray imaging units 403 but to sequentially establish the communication with the plural X-ray imaging units.

When the second communication unit 703 operates as the master unit and the first communication unit 503 operates as the slave unit, the second communication unit 703 starts the X-ray imaging control unit 401 as the master unit, by using the SSID and the encryption key obtained by the wireless configuration information managing unit 701. On the other hand, the first communication unit 503 searches for the master unit by using the SSID and the encryption key obtained by the wireless configuration information managing unit 701, and thus establishes the communication with the master unit. After the communication is established, a control command and the like from the X-ray imaging control unit 401 are input from the second communication unit 703 to the X-ray imaging unit 403 via the first communication unit 503. The X-ray imaging unit 403 comes into the state capable of performing imaging of an X-ray image, based on the control command. After then, X-rays are irradiated, the X-ray image is imaged by the X-ray imaging unit 403, and the digital data of the X-ray image is thus generated. Then, the digital data of the X-ray image is transmitted from the first communication unit 503 to the X-ray imaging control unit 401 via the second communication unit 703. The X-ray imaging control unit 401 performs processes to the digital data of the X-ray image, and displays the X-ray image on the operation display unit 402.

When the wireless configuration information managing unit 701 individually manages the wireless configuration information for each of the plural X-ray imaging units 403 and the second communication unit 703 operates as the master unit, the second communication unit 703 can simultaneously establish the communication with the plural X-ray imaging units 403.

Moreover, when the second communication unit 703 operates as the master unit, the X-ray imaging control unit 401 and the X-ray imaging unit 403 may perform the wireless communication with each other by using the master (e.g., the HIS/RIS terminal 405) wire-connected to the X-ray imaging control unit 401.

Incidentally, the communication means between the wireless configuration information notifying unit 505 and the wireless configuration information receiving unit 501 may be a wired communication means using a LAN cable or the like, a communication means using infrared communication, or a wireless communication means using Bluetooth™ communication. When the wired communication means using the LAN cable is used, for example, the X-ray imaging units 403a and 403b can be connected to the hospital LAN 404 in the configuration illustrated in FIG. 4.

As just described, in the present embodiment, the X-ray imaging control unit 401 manages the configuration information indicating, in addition to whether the X-ray imaging unit 403 operates as the master unit or the slave unit, whether the X-ray imaging control unit 401 operates as the master unit or the slave unit. Therefore, it is possible to facilitate handling of the X-ray imaging system. More specifically, it is possible to make the transportability of the apparatus constituting the X-ray imaging system easy, and it is possible to easily increase and decrease the number of the X-ray imaging units 403. Besides, when the X-ray imaging control unit 401 is operated as the master unit and the two or more X-ray imaging units 403 are operated as the slave units, it becomes unnecessary to switch the X-ray imaging unit 403 to be connected to the X-ray imaging control unit 401. Moreover, in such a case, the X-ray imaging control unit 401 can simultaneously be connected to both the X-ray imaging unit 403 and the hospital LAN master unit.

Third Embodiment

Subsequently, the third embodiment will be descried. The present embodiment has been accomplished by adding, to the second embodiment, the configuration in which the X-ray imaging control unit 401 communicates with an apparatus connected to the hospital LAN 404. Therefore, in the present embodiment, the portions same as those already described in the first and second embodiments are respectively denoted by the corresponding same reference numerals illustrated in FIGS. 5 to 8, and the detailed descriptions thereof will be omitted.

Figure 9:
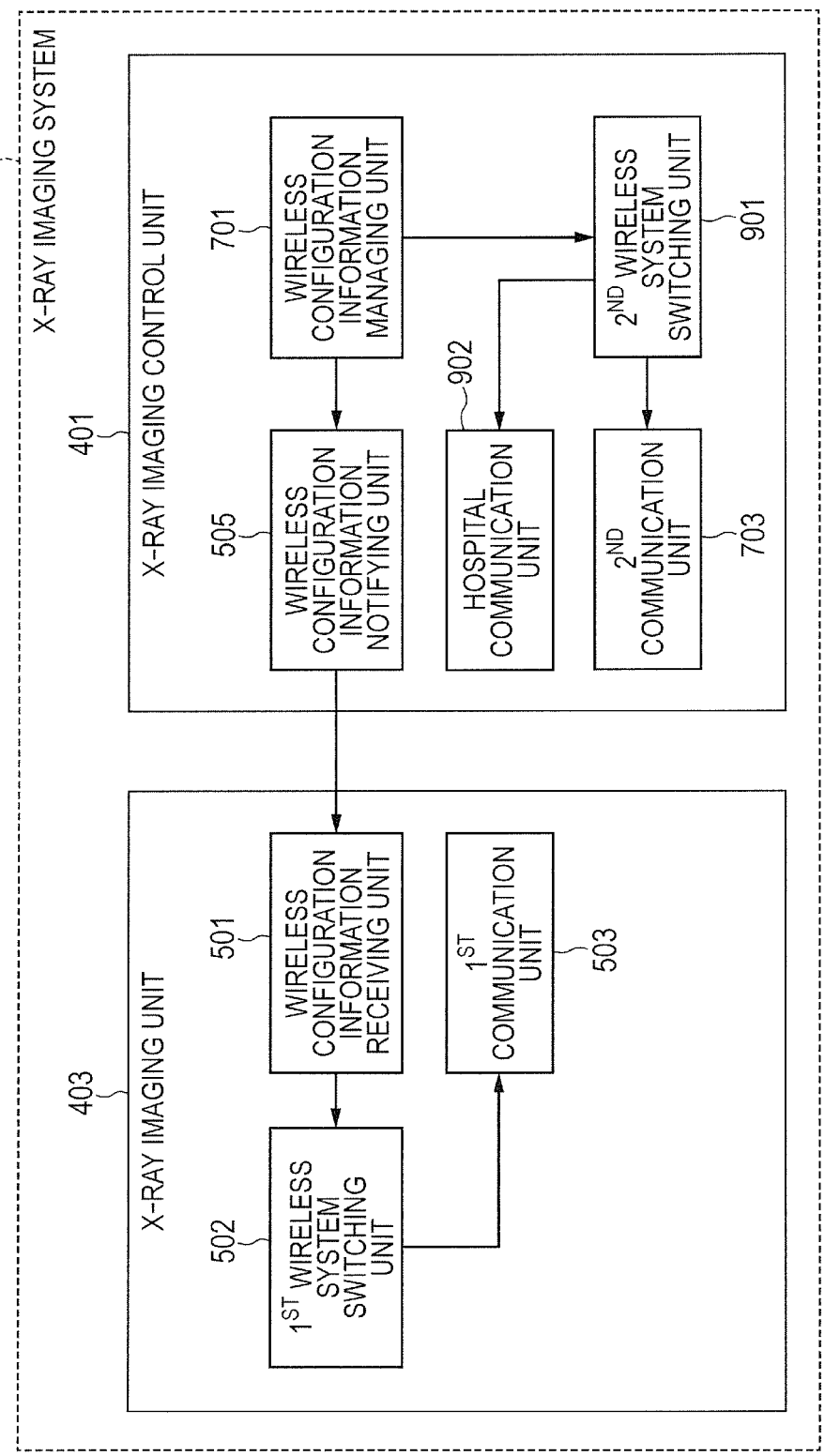
FIG. 9 is a block diagram for illustrating a sixth example of the X-ray imaging system.

FIG. 9 is a block diagram for illustrating an example of the configuration of an X-ray imaging system 900 according to the present embodiment. The X-ray imaging system 900 of FIG. 9 comprises the X-ray imaging control unit 401 and the X-ray imaging unit 403. The X-ray imaging unit 403 comprises the wireless configuration information receiving unit 501, the first wireless system switching unit 502 and the first communication unit 503. The X-ray imaging control unit 401 comprises the wireless configuration information notifying unit 505, the wireless configuration information managing unit 701, the second communication unit 703, a second wireless system switching unit 901 and a hospital communication unit 902.

Figure 10:
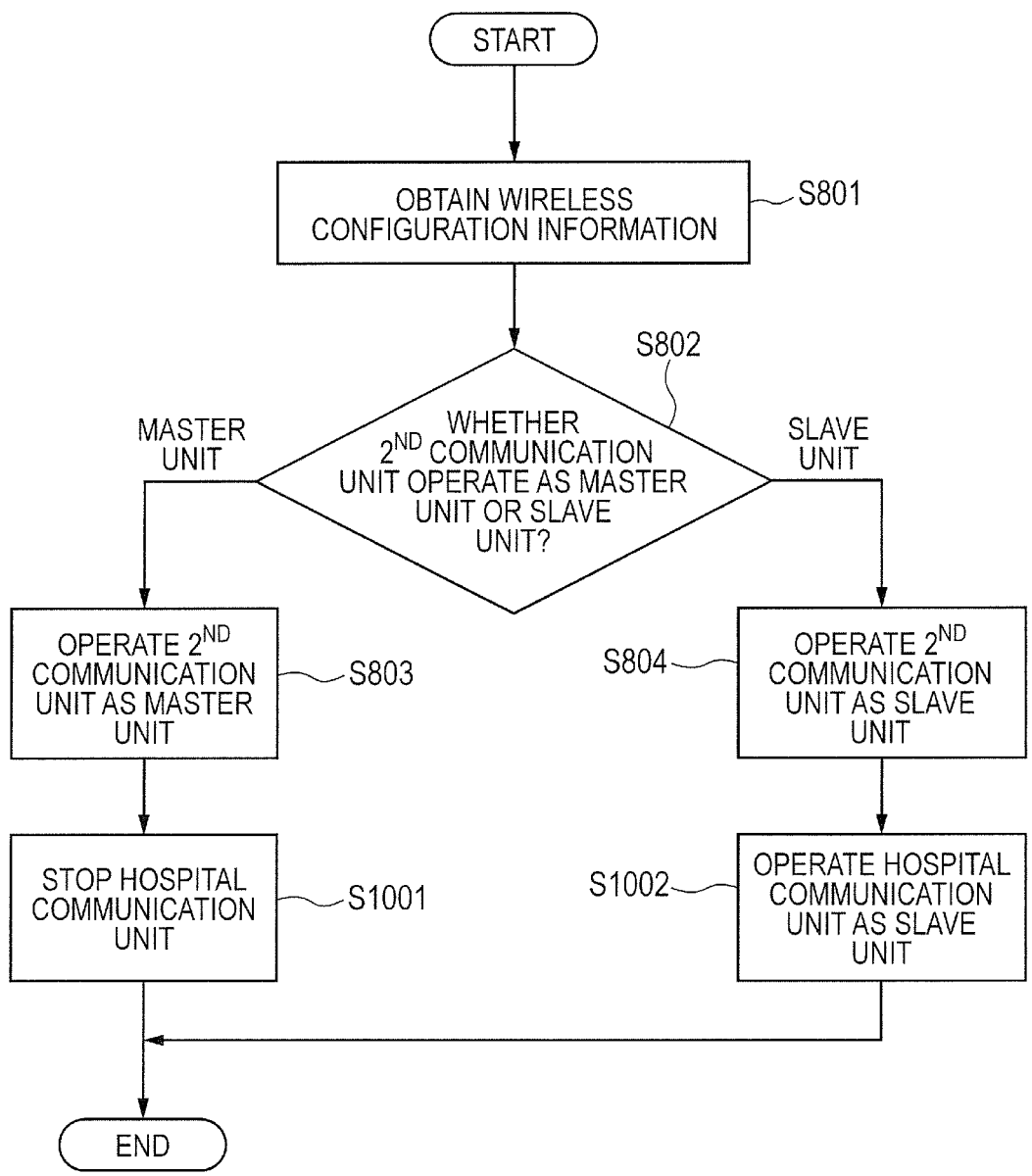
FIG. 10 is a flow chart for describing a third example of the operation of the X-ray imaging system.

FIG. 10 is a flow chart for describing an example of the operation of the X-ray imaging system 900. Hereinafter, the examples of the configuration and the process of the X-ray imaging system 900 will be described with reference to FIGS. 9 and 10.

Here, since the operation of the X-ray imaging system 900 at the time when switching the operation of the first communication unit 503 is achieved by the operation in S601 to S606 of FIG. 6 described in the first embodiment, the detailed description thereof will be omitted. Since the wireless configuration information managing unit 701 of the X-ray imaging control unit 401 manages the wireless configuration information described in the second embodiment, the detailed description of the wireless configuration information will be omitted. The operation of the X-ray imaging system 900 at the time of switching the operation of the second communication unit 703 is as below.

The second wireless system switching unit 901 obtains the wireless configuration information from the wireless configuration information managing unit 701 (S801). Next, the second wireless system switching unit 901 determines whether the second communication unit 703 operates as the master unit or the slave unit, based on the wireless configuration information obtained in S801 (S802). Then, when the second communication unit 703 operates as the master unit, the second wireless system switching unit 901 sets the second communication unit 703 to operate as the master unit (S803). Then, the second wireless system switching unit 901 stops the operation of the hospital communication unit 902 (S1001). Here, the hospital communication unit 902 is used to communicate with the external apparatuses such as the HIS/RIS terminal 405, the storage server 406, the image inspection WS 407 and the like respectively connected to the hospital LAN 404.

As previously described with reference to FIG. 3, the X-ray imaging control unit 401 is connected to the hospital LAN 404 by using the wireless slave unit. The X-ray imaging control unit 401 (the hospital communication unit 902) can be connected to the hospital LAN 404. However, if the communication with the hospital LAN 404 is once disconnected, the communication by the wireless master unit of the second communication unit 703 is once disconnected when the hospital communication unit 902 searches for the master unit. Thus, to prevent such communication disconnection by the second communication unit 703, in the present embodiment, the operation of the hospital communication unit 902 is stopped in S1001 when the second communication unit 703 operates as the master unit.

On the other hand, when the second communication unit 703 operates as the slave unit in S802, the second wireless system switching unit 901 sets the second communication unit 703 to operate as the slave unit (S804). Next, the second wireless system switching unit 901 sets the hospital communication unit 902 to operate as the slave unit (S1002).

As just described, the case where the second communication unit 703 operates as the master unit has the advantage over the case where the second communication unit 703 operates as the salve unit, because it is possible in the former case to simultaneously establish the communication with the plural X-ray imaging units 403. On the other hand, the case where the second communication unit 703 operates as the slave unit has the advantage over the case where the second communication unit 703 operates as the master unit, because it is possible in the former case to certainly perform the simultaneous communication with the X-ray imaging unit 403 and the hospital LAN 404.

Therefore, for example, when a user wishes to certainly achieve the connection of the X-ray imaging control unit 401 to the hospital LAN 404 by using only the one X-ray imaging unit 403, the configuration information is set to operate the second communication unit 703 as the slave unit. On the other hand, when it is allowed to connect the X-ray imaging control unit 401 to the hospital LAN 404 after the imaging by using the plural X-ray imaging units 403, the configuration information is set to operate the second communication unit 703 as the master unit. As just described, in the present embodiment, in addition to the effect described in the second embodiment, there is a further effect that it is possible to properly determine whether to operate the second communication unit 703 as the master unit or the slave unit according to a use case.

Fourth Embodiment

Subsequently, the fourth embodiment will be descried. The present embodiment has been accomplished by adding, to the second embodiment, the configuration for obtaining a radio wave reception situation. Therefore, in the present embodiment, the portions same as those already described in the first to third embodiments are respectively denoted by the corresponding same reference numerals illustrated in FIGS. 5 to 10, and the detailed descriptions thereof will be omitted.

Figure 11:
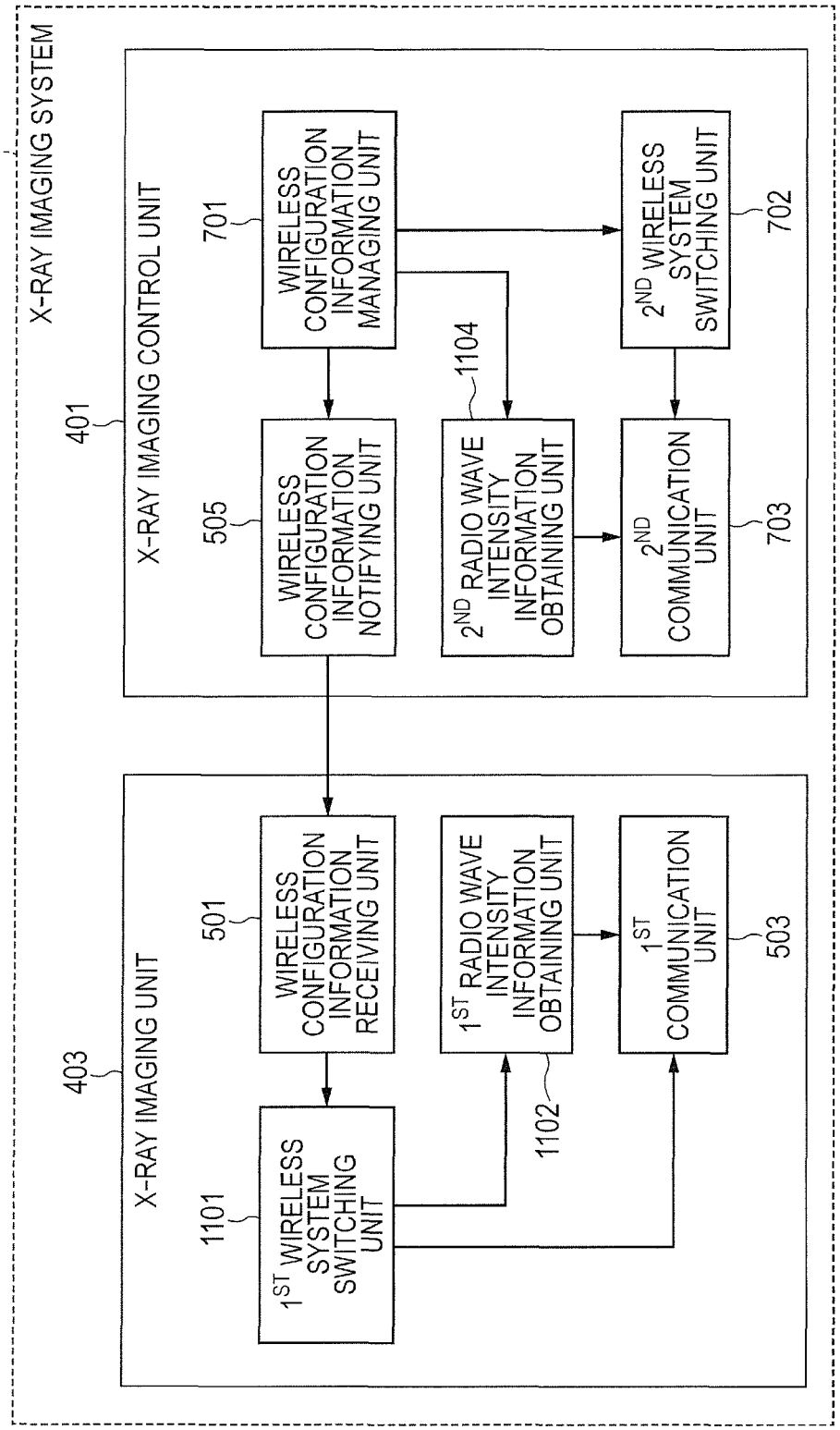
FIG. 11 is a block diagram for illustrating a seventh example of the X-ray imaging system.

FIG. 11 is a block diagram for illustrating an example of an X-ray imaging system 1100 according to the present embodiment. The X-ray imaging system 1100 of FIG. 11 comprises the X-ray imaging control unit 401 and the X-ray imaging unit 403. The X-ray imaging unit 403 comprises the wireless configuration information receiving unit 501, the first communication unit 503, a first wireless system switching unit 1101 and a first radio wave intensity information obtaining unit 1102. The X-ray imaging control unit 401 comprises the wireless configuration information notifying unit 505, the wireless configuration information managing unit 701, the second wireless system switching unit 702, the second communication unit 703 and a second radio wave intensity information obtaining unit 1104.

Figure 12:
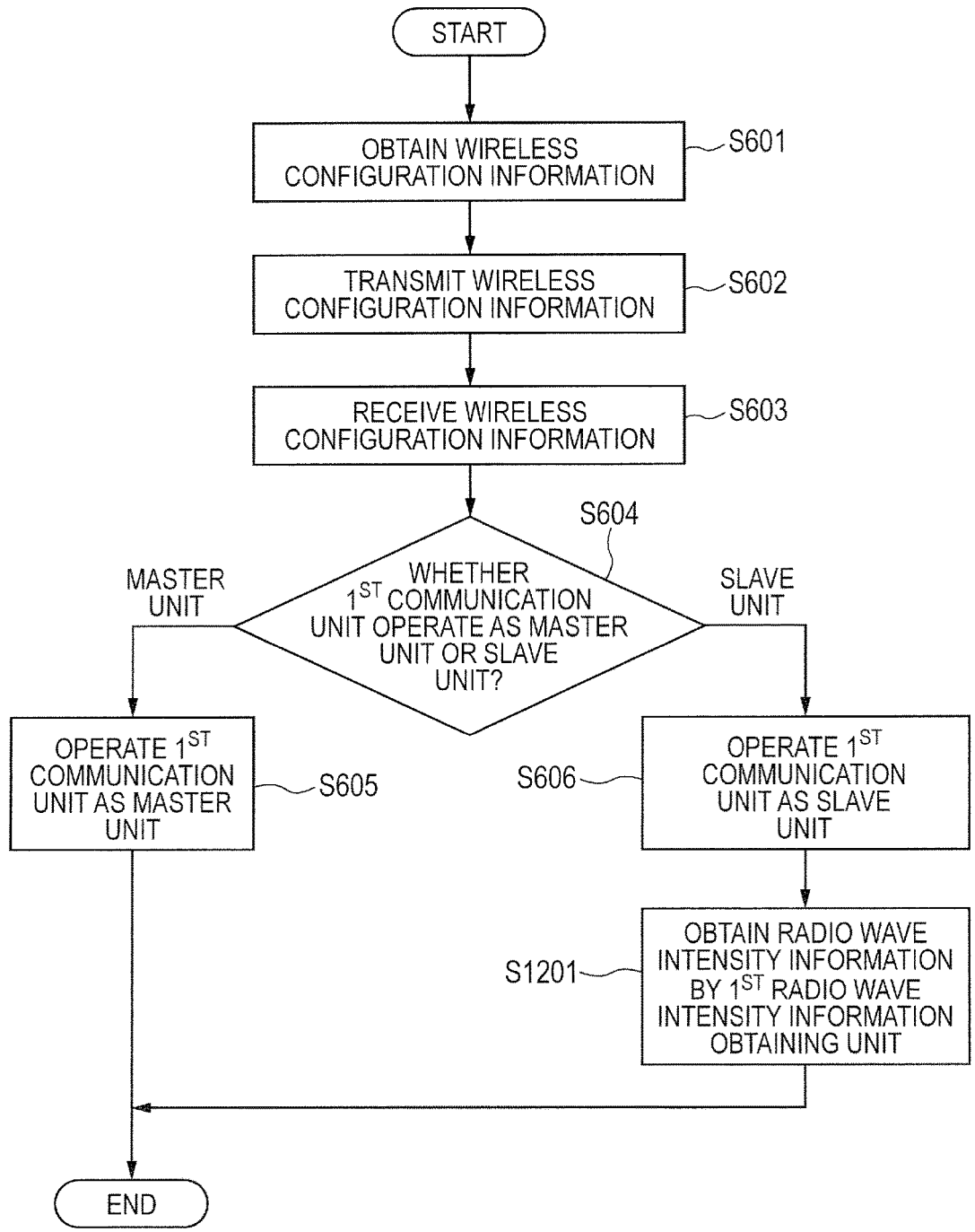
FIG. 12 is a flow chart for describing a fourth example of the operation of the X-ray imaging system.
Figure 13:
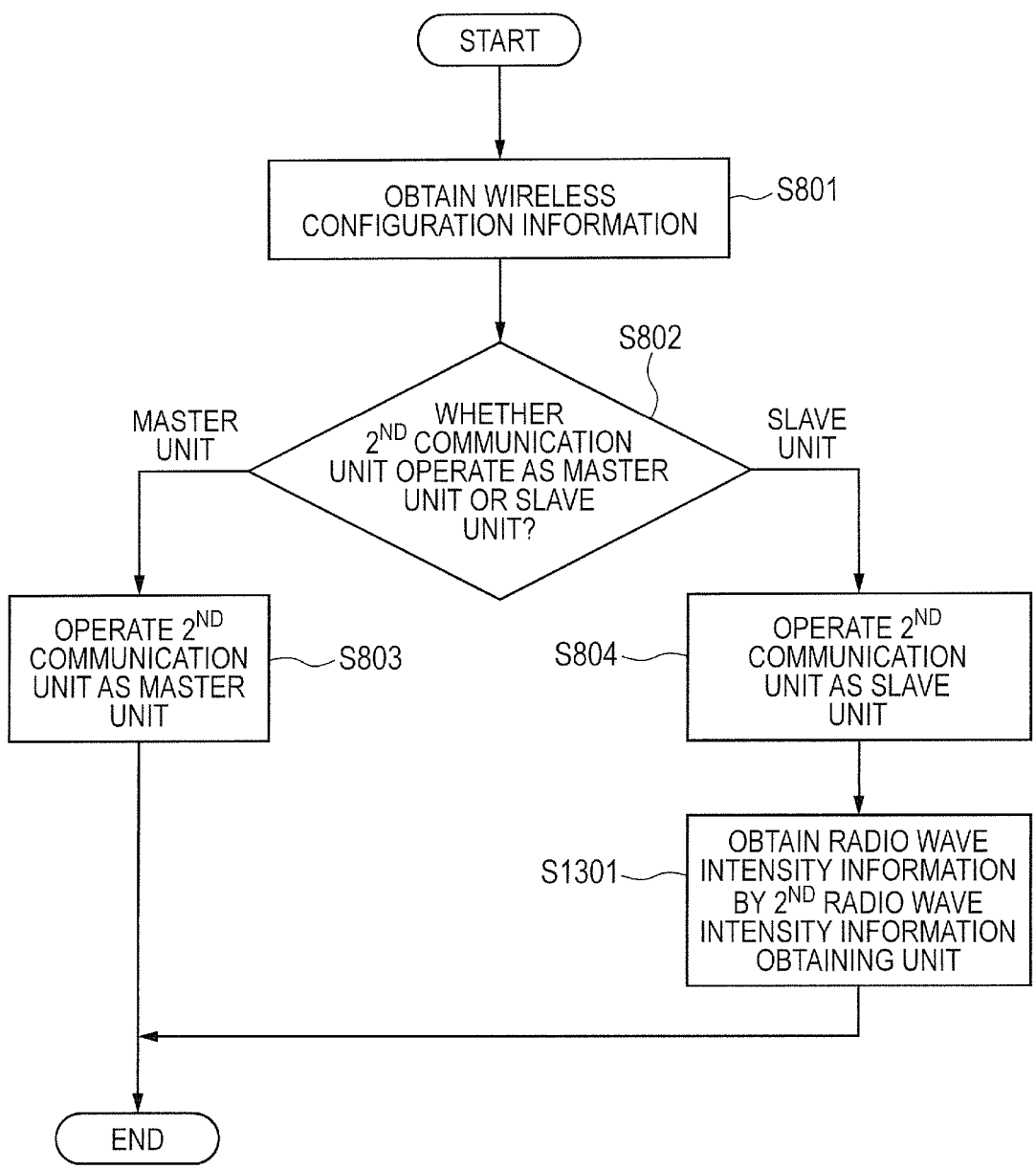
FIG. 13 is a flow chart for describing a fifth example of the operation of the X-ray imaging system.

FIGS. 12 and 13 are flow charts for describing an example of the operation of the X-ray imaging system 1100. Hereinafter, the examples of the configuration and the process of the X-ray imaging system 1100 will be described with reference to FIGS. 11 to 13.

Here, the operation of the X-ray imaging system 1100 (the operation of the X-ray imaging unit 403) at the time when switching the operation of the first communication unit 503 is achieved by adding a process in S1201 to the operation in S601 to S606 in the flow chart of FIG. 6.

That is, when it is determined in S604 that the first communication unit 503 operates as the slave unit, the first wireless system switching unit 1101 sets the first communication unit 503 to operate as the slave unit (S606). Then, the first radio wave intensity information obtaining unit 1102 obtains radio wave intensity information indicating a reception intensity of the radio wave in the X-ray imaging unit 403 (S1201). As just described, in the present embodiment, the first radio wave intensity information obtaining unit 1102 obtains the radio wave intensity information when the first communication unit 503 operates as the slave unit, and does not obtain the radio wave intensity information when the first communication unit 503 operates as the master unit.

The operation of the X-ray imaging system 1100 (the operation of the X-ray imaging control unit 401) at the time when switching the operation of the second communication unit 703 is achieved by adding a process in S1301 to the operation in S801 to S804 in the flow chart of FIG. 8.

That is, when it is determined in S802 that the second communication unit 703 operates as the slave unit, the second wireless system switching unit 702 sets the second communication unit 703 to operate as the slave unit (S804). Then, the second radio wave intensity information obtaining unit 1104 obtains radio wave intensity information indicating a reception intensity of the radio wave in the X-ray imaging control unit 401 (S1301). As just described, in the present embodiment, the second radio wave intensity information obtaining unit 1104 obtains the radio wave intensity information when the second communication unit 703 operates as the slave unit, and does not obtain the radio wave intensity information when the first communication unit 503 operates as the master unit.

Since the radio wave intensity information can be obtained only on the side of the slave unit and it is necessary to properly obtain the radio wave intensity information according to the constitution of the wireless configuration information managing unit 701, the operations as indicated by the flow charts of FIGS. 12 and 13 are performed.

In the present embodiment, the case where the radio wave intensity information is the information indicating the reception intensity of the radio wave has been described as the example. However, the radio wave intensity information like this need not necessarily be used if the information to be used indicates a radio wave reception situation. For example, information indicating stability of a radio wave may be used in addition to or instead of the radio wave intensity information.

Incidentally, it may be possible to add the hospital communication unit 902 described in the third embodiment to the X-ray imaging control unit 401 of the present embodiment.

Fifth Embodiment

Subsequently, the fifth embodiment will be descried. The present embodiment has been accomplished by adding, to the fourth embodiment, the configuration that the X-ray imaging unit 403 displays radio wave intensity information. Therefore, in the present embodiment, the portions same as those already described in the first to fourth embodiments are respectively denoted by the corresponding same reference numerals illustrated in FIGS. 5 to 13, and the detailed descriptions thereof will be omitted.

Figure 14:
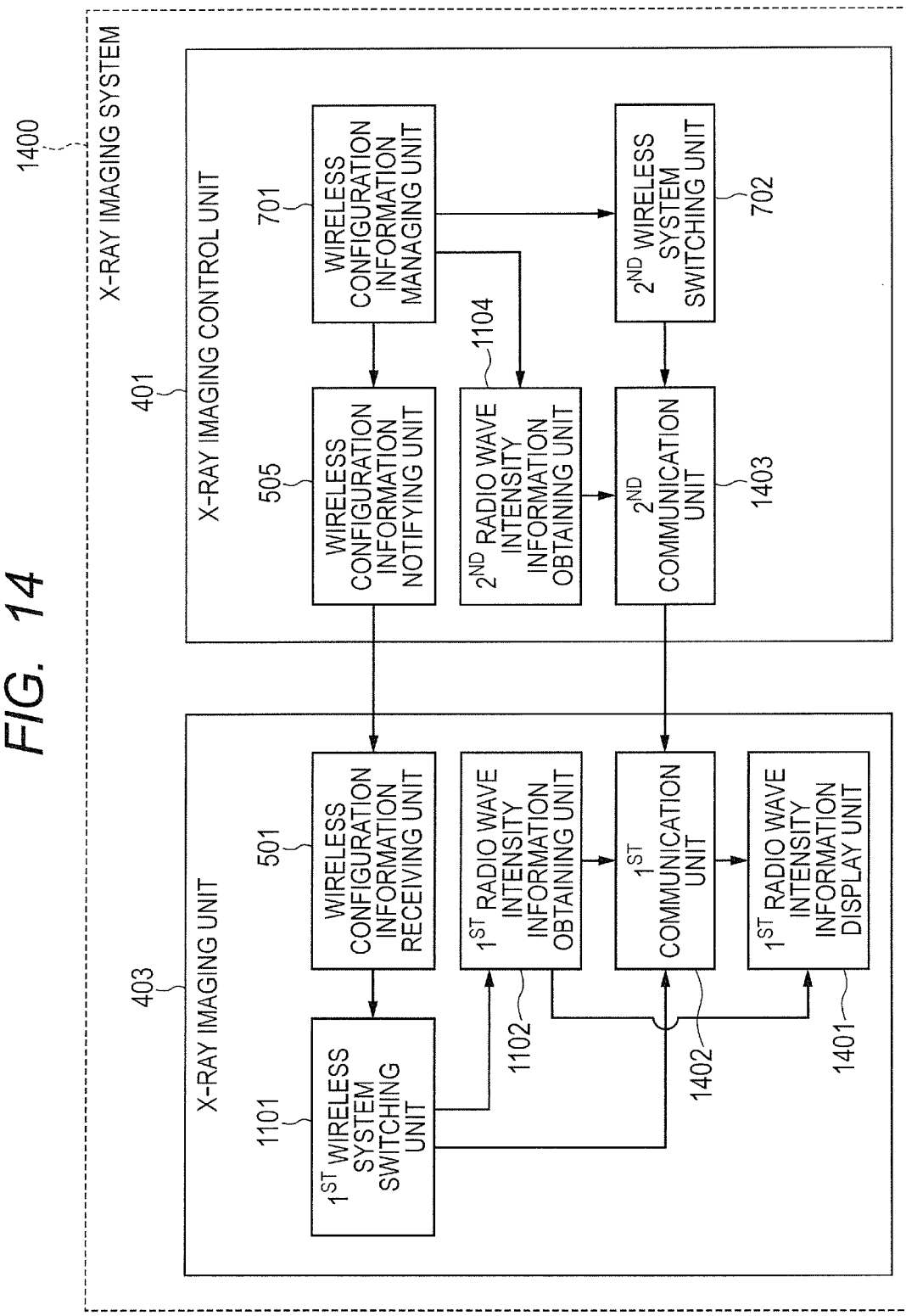
FIG. 14 is a block diagram for illustrating an eighth example of the X-ray imaging system.

FIG. 14 is a block diagram for illustrating an example of the configuration of an X-ray imaging system 1400 according to the present embodiment. The X-ray imaging system 1400 of FIG. 14 comprises the X-ray imaging control unit 401 and the X-ray imaging unit 403. The X-ray imaging unit 403 comprises the wireless configuration information receiving unit 501, the first wireless system switching unit 1101, the first radio wave intensity information obtaining unit 1102, a first radio wave intensity information display unit 1401 and a first communication unit 1402. The X-ray imaging control unit 401 comprises the wireless configuration information notifying unit 505, the wireless configuration information managing unit 701, the second wireless system switching unit 702, the second radio wave intensity information obtaining unit 1104 and a second communication unit 1403.

Figure 15:
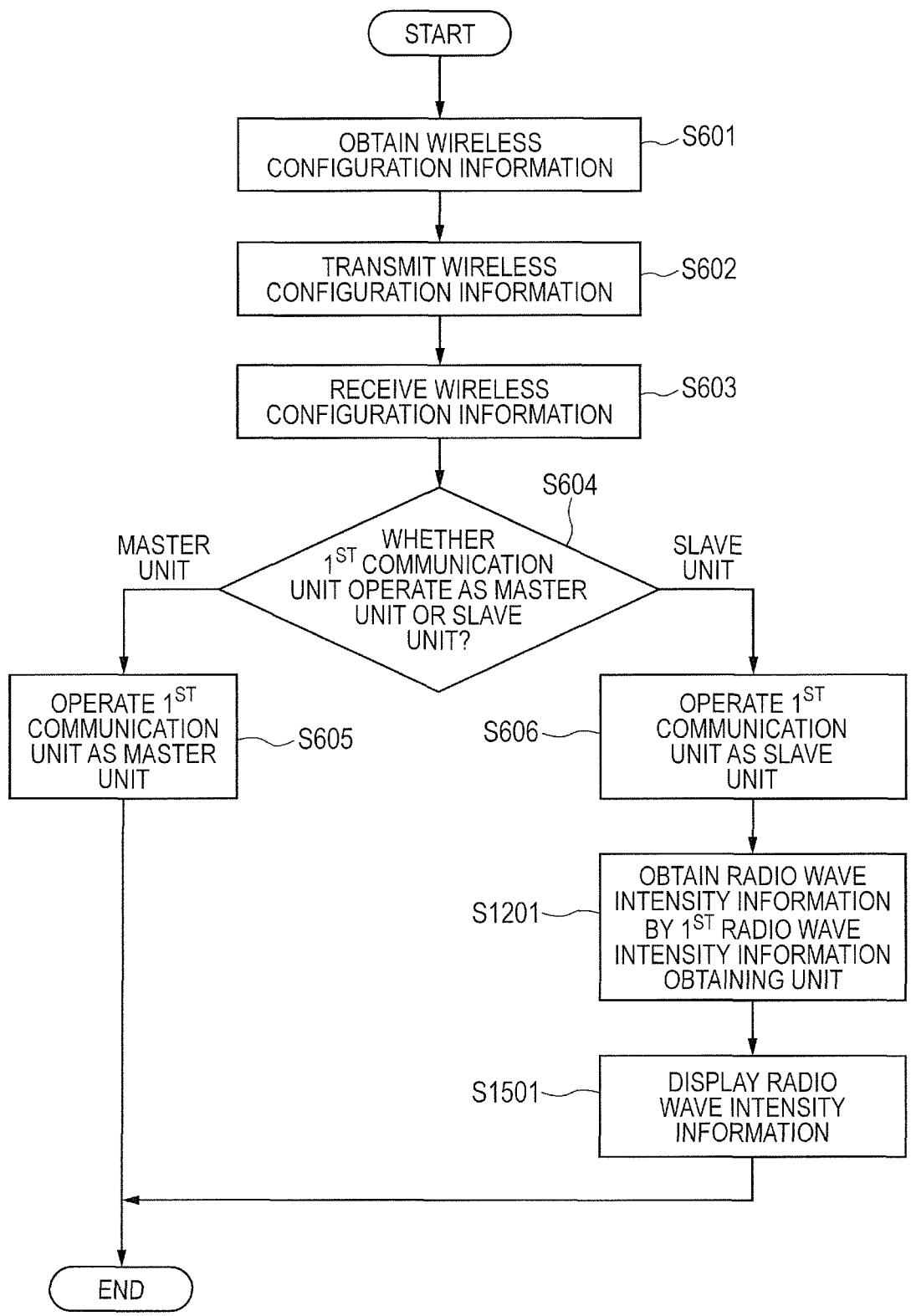
FIG. 15 is a flow chart for describing a sixth example of the operation of the X-ray imaging system.
Figure 16:
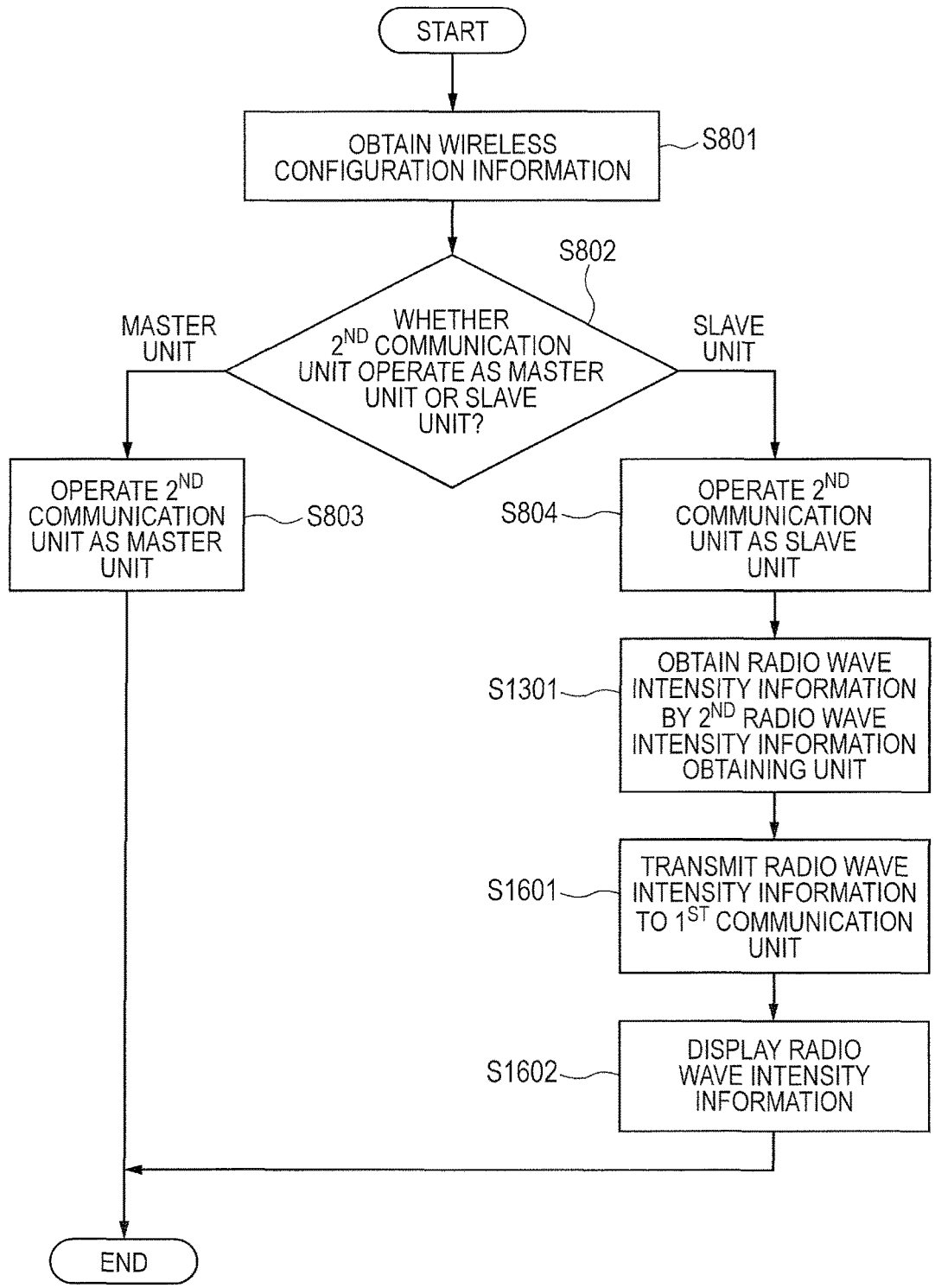
FIG. 16 is a flow chart for describing a seventh example of the operation of the X-ray imaging system.

FIGS. 15 and 16 are flow charts for describing an example of the operation of the X-ray imaging system 1400. Hereinafter, the examples of the configuration and the process of the X-ray imaging system 1400 will be described with reference to FIGS. 14 to 16.

Here, the operation of the X-ray imaging system 1100 (the operation of the X-ray imaging unit 403) at the time when switching the operation of the first communication unit 1402 is achieved by adding a process in S1501 to the operation in S601 to S606 and S1201 indicated by the flow chart of FIG. 12.

That is, when the first radio wave intensity information obtaining unit 1102 obtains the radio wave intensity information in S1201, the first radio wave intensity information display unit 1401 displays in S1501 the radio wave intensity information obtained in S1201. As just described, in the present embodiment, the first radio wave intensity information display unit 1401 displays the radio wave intensity information obtained by the first radio wave intensity information obtaining unit 1102, when the second communication unit 1403 operates as the slave unit. On the other hand, the first radio wave intensity information obtaining unit 1102 does not obtain the radio wave intensity information, when the second communication unit 1403 operates as the master unit.

The operation of the X-ray imaging system 1400 at the time when switching the operation of the second communication unit 1403 is achieved by adding processes of S1601 and S1602 to the operation in S801 to S804 and S1301 indicated by the flow chart of FIG. 13.

That is, when the second radio wave intensity information obtaining unit 1104 obtains the radio wave intensity information in S1301, the second communication unit 1403 transmits in S1601 the radio wave intensity information obtained in S1301 to the first communication unit 1402. Next, in S1602, the first radio wave intensity information display unit 1401 displays the radio wave intensity information transmitted in S1601. As just described, in the present embodiment, the first radio wave intensity information display unit 1401 displays the radio wave intensity information transmitted from the second communication unit 1403 on the first radio wave intensity information display unit 1401, when the second communication unit 1403 operates as the slave unit. On the other hand, the second communication unit 1403 does not transmit the radio wave intensity information, when the second communication unit 1403 operates as the master unit.

The method of displaying the radio wave intensity information is not specifically limited. For example, it is possible to directly display the reception intensity itself indicated in the radio wave intensity information obtained in S1201. Besides, it is possible to display the reception intensity indicated in the radio wave intensity information obtained in S1201, on percentage (i.e., the percentage of the reception intensity indicated in the radio wave intensity information to the maximum value). It may be possible to display to which level in preset plural levels the reception intensity indicated in the radio wave intensity information obtained in S1201 belongs.

By the above constitution, even if the master and slave relationship between the X-ray imaging control unit 401 and the X-ray imaging unit 403 is changed in the configuration information managed by the wireless configuration information managing unit 701, it is possible to display the radio wave intensity information to the user in the same display form.

Incidentally, as described in the fourth embodiment, the display form of the radio wave intensity information is not specifically limited. Besides, as described in the fourth embodiment, the radio wave intensity information like this need not necessarily be used if the information indicating the radio wave reception situation is used.

Sixth Embodiment

Subsequently, the sixth embodiment will be descried. The present embodiment has been accomplished by adding, to the fourth embodiment, the configuration that the X-ray imaging control unit 401 displays the radio wave intensity information. Therefore, in the present embodiment, the portions same as those already described in the first to fourth embodiments are respectively denoted by the corresponding same reference numerals illustrated in FIGS. 5 to 13, and the detailed descriptions thereof will be omitted.

Figure 17:
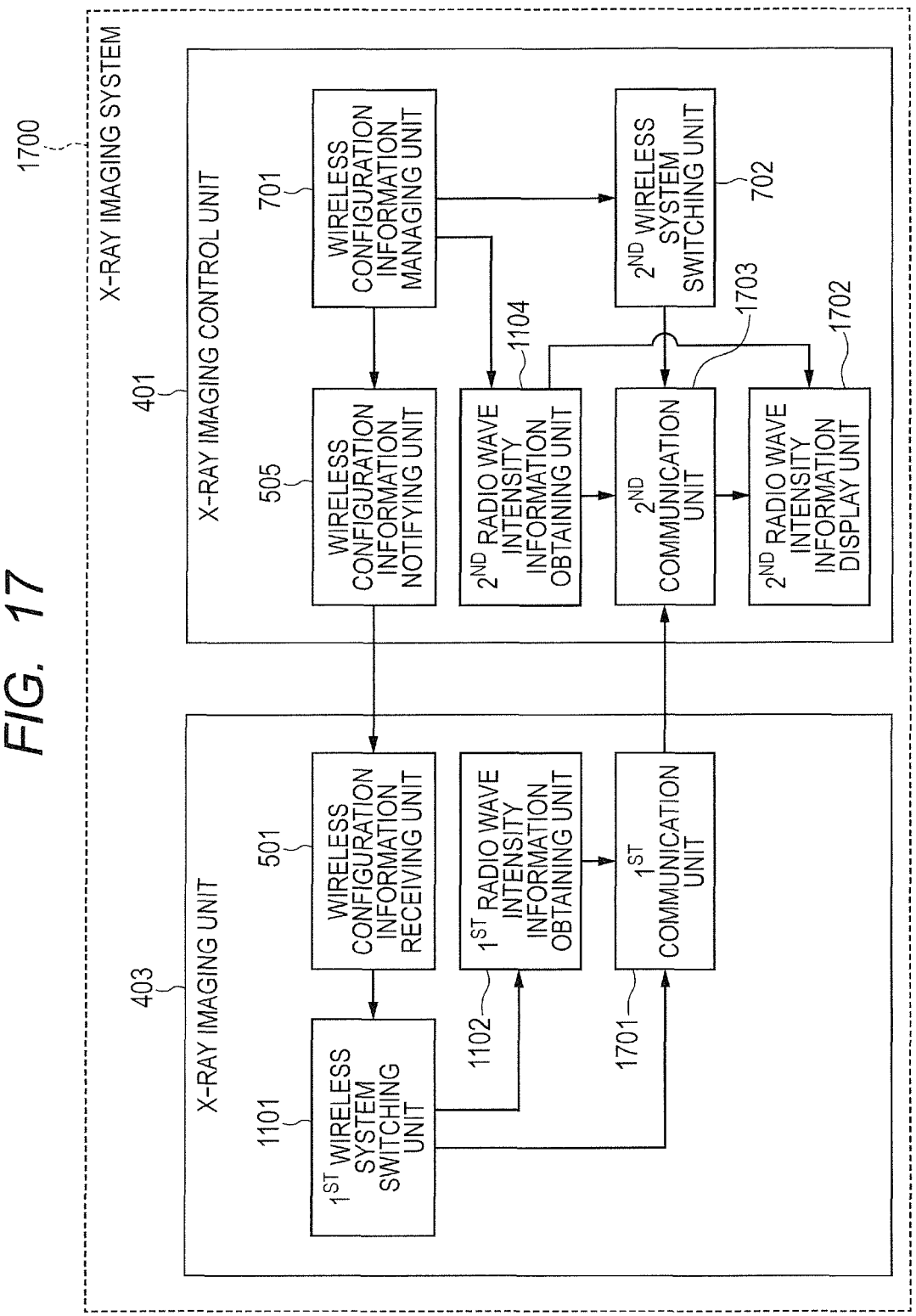
FIG. 17 is a block diagram for illustrating a ninth example of the X-ray imaging system.

FIG. 17 is a block diagram for illustrating an example of the configuration of an X-ray imaging system 1700 according to the present embodiment. The X-ray imaging system 1700 of FIG. 17 comprises the X-ray imaging control unit 401 and the X-ray imaging unit 403. The X-ray imaging unit 403 comprises the wireless configuration information receiving unit 501, the first wireless system switching unit 1101, the first radio wave intensity information obtaining unit 1102 and a first communication unit 1701. The X-ray imaging control unit 401 comprises the wireless configuration information notifying unit 505, the wireless configuration information managing unit 701, the second wireless system switching unit 702, the second radio wave intensity information obtaining unit 1104, a second radio wave intensity information display unit 1702 and a second communication unit 1703.

Figure 18:
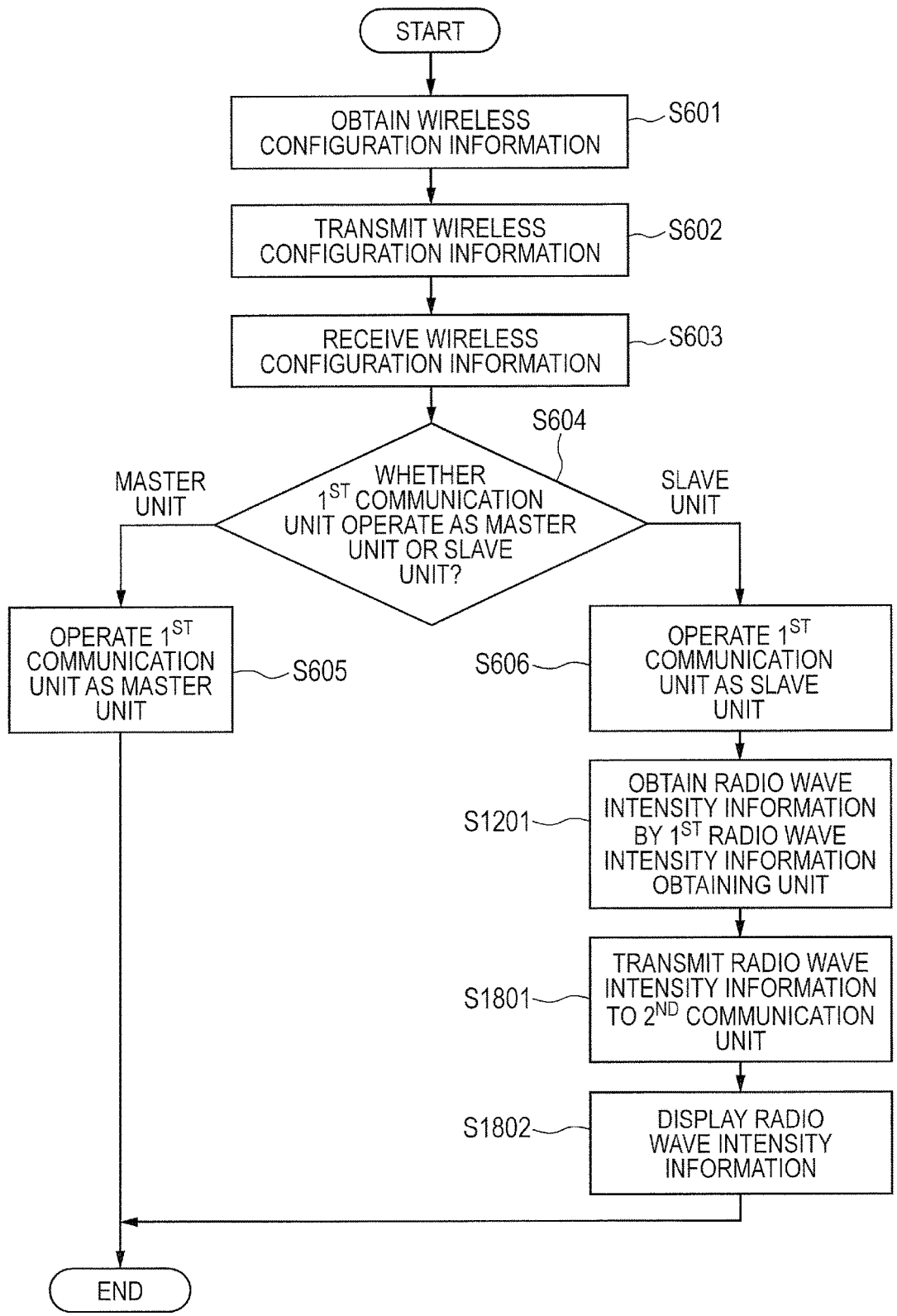
FIG. 18 is a flow chart for describing an eighth example of the operation of the X-ray imaging system.
Figure 19:
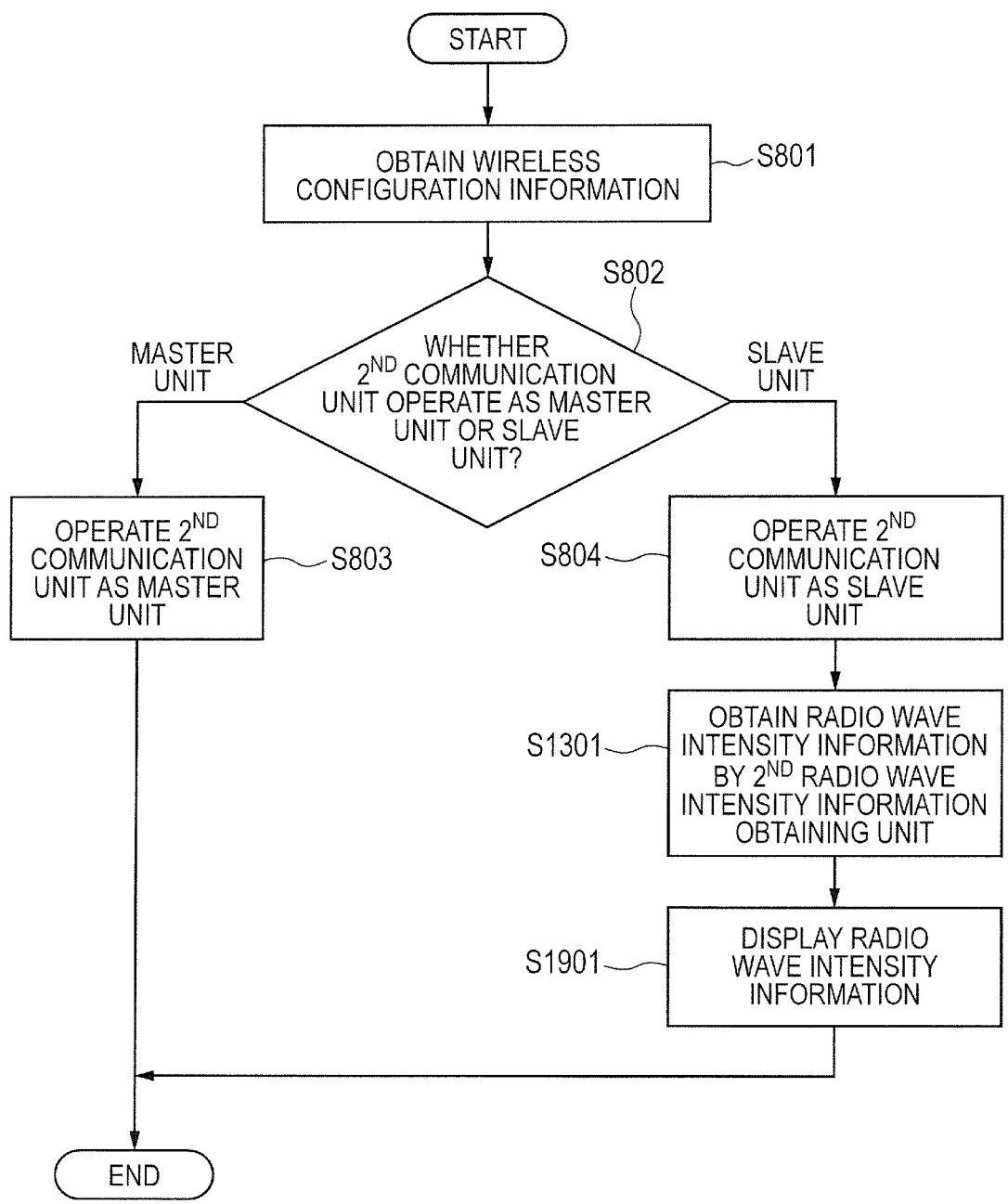
FIG. 19 is a flow chart for describing a ninth example of the operation of the X-ray imaging system.

FIGS. 18 and 19 are flow charts for describing an example of the operation of the X-ray imaging system 1700. Hereinafter, the examples of the configuration and the process of the X-ray imaging system 1700 will be described with reference to FIGS. 17 to 19.

Here, the operation of the X-ray imaging system 1700 at the time when switching the operation of the first communication unit 1402 is achieved by adding processes of S1801 and S1802 to the operation in S601 to S606 and S1201 indicated by the flow chart of FIG. 12.

That is, when the first radio wave intensity information obtaining unit 1102 obtains the radio wave intensity information in S1201, the first communication unit 1701 transmits in S1801 the radio wave intensity information obtained in S1201 to the second communication unit 1703. Next, in S1802, the second radio wave intensity information display unit 1702 displays the radio wave intensity information transmitted in S1601. As just described, in the present embodiment, the second radio wave intensity information display unit 1702 displays the radio wave intensity information received from the first communication unit 1701, when the first communication unit 1701 operates as the slave unit. On the other hand, the first communication unit 1701 does not transmit the radio wave intensity information, when the first communication unit 1701 operates as the master unit.

The operation of the X-ray imaging system 1700 (the X-ray imaging control unit 401) at the time when switching the operation of the second communication unit 1403 is achieved by adding a process of S1901 to the operation in S801 to S804 and S1301 indicated by the flow chart of FIG. 13.

That is, when the second radio wave intensity information obtaining unit 1104 obtains the radio wave intensity information in S1301, the second radio wave intensity information display unit 1702 displays in S1901 the radio wave intensity information obtained in S1301. As just described, in the present embodiment, the second radio wave intensity information display unit 1702 displays the radio wave intensity information obtained by the second radio wave intensity information obtaining unit 1104, when the second communication unit 1703 operates as the slave unit. On the other hand, the second radio wave intensity information obtaining unit 1104 does not obtain the radio wave intensity information, when the second communication unit 1703 operates as the master unit.

By the above constitution, even if the master and slave relationship between the X-ray imaging control unit 401 and the X-ray imaging unit 403 is changed in the configuration information managed by the wireless configuration information managing unit 701, it is possible to display the radio wave intensity information to the user in the same display form.

Incidentally, as described in the fourth embodiment, the display form of the radio wave intensity information is not specifically limited. Besides, as described in the fourth embodiment, the radio wave intensity information like this need not necessarily be used if the information indicating the radio wave reception situation is used.

Incidentally, since the above embodiments merely show the examples of the concretization when carrying out the present invention, the technical scope of the present invention should not be construed limitedly by these embodiments. That is, the present invention can be carried out in various ways without departing from its technical scope or its main characteristics.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-072492, filed Mar. 31, 2015, which is hereby incorporated by reference herein in its entirety.

What is claimed is:

1. A radiation imaging control apparatus comprising:
a managing unit configured to, in a case where a radiation imaging apparatus performs wireless communication, manage whether to operate the radiation imaging control apparatus controlling the radiation imaging apparatus as a master unit or a slave unit; and
an obtaining unit configured to, in a case where the radiation imaging control apparatus operates as the slave unit when performing the wireless communication with the radiation imaging apparatus, obtain reception information of radio wave in the radiation imaging control apparatus,
wherein at least one of the managing unit and the obtaining unit is implemented by a central processing unit, a memory and a communication circuit.

2. The radiation imaging control apparatus according to claim 1, wherein the wireless configuration information includes the information indicating whether to operate the radiation imaging apparatus as the master unit or the slave unit when the radiation imaging apparatus performs the wireless communication with the radiation imaging control apparatus, and information indicating whether to operate the radiation imaging control apparatus as a master unit or a slave unit when the radiation imaging control apparatus performs wireless communication with the radiation imaging apparatus.

3. The radiation imaging control apparatus according to claim 2, wherein the wireless configuration information is set such that one of the radiation imaging apparatus and the radiation imaging control apparatus operates as the master unit and the other thereof operates as the slave unit.

4. The radiation imaging control apparatus according to claim 2, further comprising a selecting unit configured to select whether to operate the radiation imaging control apparatus as the master unit or the slave unit when performing the wireless communication with the radiation imaging apparatus, based on the wireless configuration information managed by the managing unit,
wherein the selecting unit is implemented by the processor.

5. The radiation imaging control apparatus according to claim 4, wherein the selecting unit is configured to select to operate the radiation imaging control apparatus as the master unit and utilize an apparatus wire-connected to the radiation imaging control apparatus, when performing the wireless communication with the radiation imaging apparatus.

6. The radiation imaging control apparatus according to claim 4, further comprising a stopping unit configured to, in a case where it is selected by the selecting unit to operate the radiation imaging control apparatus as the master unit when performing the wireless communication with the radiation imaging apparatus, stop communication with an external apparatus mutually communicably connected to the radiation imaging control apparatus via a network,
wherein the stopping unit is implemented by the processor.

7. The radiation imaging control apparatus according to claim 4, wherein the selecting unit is configured to select to operate the radiation imaging control apparatus as the slave unit when performing the wireless communication with the radiation imaging apparatus, and operate the radiation imaging control apparatus as the slave unit when performing communication with an external apparatus mutually communicably connected to the radiation imaging control apparatus via a network.

8. The radiation imaging control apparatus according to claim 4, further comprising a display unit configured to, in the case where it is selected by the selecting unit to operate the radiation imaging control apparatus as the slave unit when performing the wireless communication with the radiation imaging apparatus, display the information, obtained by the obtaining unit, related to the situation of the radio wave reception in the radiation imaging control apparatus.

9. The radiation imaging control apparatus according to claim 4, further comprising a transmitting unit configured to, in the case where it is selected by the selecting unit to operate the radiation imaging control apparatus as the slave unit when performing the wireless communication with the radiation imaging apparatus, transmit the information, obtained by the obtaining unit, related to the situation of the radio wave reception in the radiation imaging control apparatus to the radiation imaging apparatus.

10. A radiation imaging apparatus comprising:
a selecting unit configured to, in a case where the radiation imaging apparatus performs wireless communication with an external apparatus, select whether to operate the radiation imaging apparatus as a master unit or a slave unit; and
an obtaining unit configured to, in a case where the radiation imaging apparatus is selected by the selecting unit to operate as the slave unit, obtain reception information of radio wave in the radiation imaging apparatus,
wherein at least one of the selecting unit and the obtaining unit is implemented by a central processing unit, a memory and a communication circuit.

11. The radiation imaging apparatus according to claim 10, further comprising a display unit configured to, in the case where it is selected by the selecting unit to operate the radiation imaging apparatus as the slave unit, display the information, obtained by the obtaining unit, related to the situation of the radio wave reception in the radiation imaging apparatus,
wherein the display unit is implemented by the processor.

12. The radiation imaging apparatus according to claim 10, further comprising a transmitting unit configured to, in the case where it is selected by the selecting unit to operate the radiation imaging apparatus as the slave unit, transmit by the wireless communication the information, obtained by the obtaining unit, related to the situation of the radio wave reception in the radiation imaging apparatus to a radiation imaging control apparatus of controlling the radiation imaging apparatus.

13. A storage medium of storing a non-transitory computer-readable program for causing a computer to function as each unit of a radiation imaging control apparatus comprising:
a managing unit configured to, in a case where a radiation imaging apparatus performs wireless communication, manage whether to operate the radiation imaging control apparatus controlling the radiation imaging apparatus as a master unit or a slave unit; and
an obtaining unit configured to, in a case where the radiation imaging control apparatus operates as the slave unit when performing the wireless communication with the radiation imaging apparatus, obtain reception information of radio wave in the radiation imaging control apparatus.

14. A storage medium of storing a non-transitory computer-readable program for causing a computer to function as each unit of a radiation imaging apparatus comprising:
a selecting unit configured to, in a case where a radiation imaging apparatus performs wireless communication with an external apparatus, select whether to operate the radiation imaging apparatus as a master unit or a slave unit; and
an obtaining unit configured to, in a case where the radiation imaging apparatus operates as the slave unit, obtain reception information of radio wave in the radiation imaging apparatus.

15. A radiation imaging control apparatus comprising:
a managing unit configured to, in a case where a radiation imaging apparatus performs wireless communication, manage whether to operate the radiation imaging control apparatus controlling the radiation imaging apparatus as a master unit or a slave unit; and
an obtaining unit configured to, in a case where the radiation imaging control apparatus operates as a the slave unit when performing the wireless communication with the radiation imaging apparatus, obtain reception information of radio wave in the radiation imaging control apparatus.

16. A radiation imaging apparatus comprising:
a selecting unit configured to, in a case where the radiation imaging apparatus performs wireless communication with an external apparatus, select whether to operate the radiation imaging apparatus as a master unit or a slave unit; and
an obtaining unit configured to, in a case where the radiation imaging apparatus is selected by the selecting unit to operate as the slave unit, obtain reception information of radio wave in the radiation imaging apparatus.

* * * * *